United States Patent
Yamoah et al.

(10) Patent No.: US 8,962,314 B2
(45) Date of Patent: Feb. 24, 2015

(54) LATERAL VENTRICLE CELL COMPOSITIONS AND USE FOR TREATING NEURAL DEGENERATIVE DISEASES

(75) Inventors: Ebenezer N. Yamoah, Davis, CA (US); Dongguang Wei, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 399 days.

(21) Appl. No.: 13/131,023

(22) PCT Filed: Nov. 24, 2009

(86) PCT No.: PCT/US2009/065758
§ 371 (c)(1),
(2), (4) Date: Sep. 16, 2011

(87) PCT Pub. No.: WO2010/062905
PCT Pub. Date: Jun. 3, 2010

(65) Prior Publication Data
US 2012/0003190 A1    Jan. 5, 2012

Related U.S. Application Data

(60) Provisional application No. 61/118,403, filed on Nov. 26, 2008.

(51) Int. Cl.
| | |
|---|---|
| *C12N 5/00* | (2006.01) |
| *C12N 5/0797* | (2010.01) |
| *C12N 5/0793* | (2010.01) |
| *A61K 35/12* | (2006.01) |

(52) U.S. Cl.
CPC .............. *C12N 5/062* (2013.01); *C12N 5/0623* (2013.01); *A61K 35/12* (2013.01)
USPC .......................................... 435/325; 435/368

(58) Field of Classification Search
None
See application file for complete search history.

(56) References Cited

U.S. PATENT DOCUMENTS 7,320,872 B2    1/2008    Janson et al.

FOREIGN PATENT DOCUMENTS

WO    WO 2008/076556 A2    6/2008

OTHER PUBLICATIONS

Sahly et al., Anat. Embryol., 196:159-170, 1997.*
Chiasson et al., J. Neurosci., 19(11):4462-4471, 1999.*
Gabrion et al., Microsc Res Tech. Apr. 15, 1998;41(2):124-157.*
Alvarez-Buylla et al., "For the long run: maintaining germinal niches in the adult brain." Neuron 41: 683-686 (2004).
Bermingham et al., "Math1: an essential gene for the generation of inner ear hair cells." Science 284: 1837-1841 (1999).
Boeda et al., "A specific promoter of the sensory cells of the inner ear defined by transgenesis." Hum Mol Genet 10: 1581-1589 (2001).
Borlongan et al., "Intracerebral transplantation of porcine choroid plexus provides structural and functional neuroprotection in a rodent model of stroke." Stroke 35:2206-2210 (2004).
Breier et al., "Expression of vascular endothelial growth factor during embryonic angiogenesis and endothelial cell differentiation." Development 114:521-532 (1992).
Coleman et al., "Fate of Embryonic Stem Cells Transplanted Into the Deafened Mammalian Cochlea." Cell Transplant. 15(5): 369-380 (2006).
Doetsch et al., "Subventricular zone astrocytes are neural stem cells in the adult mammalian brain." Cell 97: 703-716 (1999).
Doyle et al., "Differentiation of adult mouse olfactory precursor cells into hair cells in vitro." Stem Cells 25: 621-627 (2007).
Emerich et al., "Extensive neuroprotection by choroid plexus transplants in excitotoxin lesioned monkeys." Neurobiol Dis 23:471-480 (2006).
Emerich et al., "In vitro exposure of cultured porcine choroid plexus epithelial cells to immunosuppressant, anti-inflammatory, and psychoactive drugs." Cell Transplant 16:435-440 (2007).
Ernfors et al., "Protection of auditory neurons from aminoglycoside toxicity by neurotrophin-3." Nat Med 2: 463-467 (1996).
Fritzsch et al., "Effects of neurotrophin and neurotrophin receptor disruption on the afferent inner ear innervation." Semin Cell Dev Biol 8: 277-284 (1997).
Gage, "Mammalian neural stem cells." Science 287: 1433-1438 (2000).
Gale et al., "FM I -43 dye behaves as a permeant blocker of the hair-cell mechanotransducer channel." J Neurosci 21 :7013-7025 (2001).
Gale et al., "Survival of bundleless hair cells and subsequent bundle replacement in the bullfrog's saccule." J Neurobiol 50: 81-92 (2002).
Glowatzki et al., "Transmitter release at the hair cell ribbon synapse." Nat Neurosci 5: 147-154 (2002).
Gurney et al,, "Blood-brain barrier disruption by stromelysin-1 facilitates neutrophil infiltration in neuroinflammation." Neurobiol Dis 23:87- 96 (2006).
Harms et al., "Maintaining GFP tissue fluorescence through bone decalcification and long-term storage." Biotechniques. 33(6):1197-1200 (2002).
Hasson et al., "Expression in cochlea and retina of myosin Vlla, the gene product defective in Usher syndrome type IB." Proc Natl Acad Sci USA 92: 9815-9819 (1995).
Hasson et al., "Unconventional myosins in inner-ear sensory epithelia." J Cell Biol 137: 1287-1307 (1997).
Hu et al., "Survival and neural differentiation of adult neural stem cells transplanted into the mature inner ear." Exp Cell Res 302: 40-47 (2005).
Huang et al., Spatiotemporal definition of neurite outgrowth, refinement and retraction in the developing mouse cochlea. Development 134: 2925-2933 (2007).
Ide et al., "Grafting of choroid plexus ependymal cells promotes the growth of regenerating axons in the dorsal funiculus of rat spinal cord: a preliminary report." Exp Neurol 167:242-251 (2001).
Ishibashi et al., "Targeted disruption of mammalian hairy and Enhancer of split homolog-1 (HES-1) leads to up-regulation of neural helix-loop-helix factors, premature neurogenesis, and severe neural tube defects." Genes Dev 9: 3136-3148 ( 1995).
Izumikawa et al., "Auditory hair cell replacement and hearing improvement by Atoh1 gene therapy in deaf mammals." Nat Med 11: 271-276 (2005).

(Continued)

*Primary Examiner* — Daniel C Gamett
(74) *Attorney, Agent, or Firm* — Foley & Lardner LLP; Antoinette F. Konski

(57) ABSTRACT

A pluripotent stem cell isolated from the lateral ventrical of the brain or choroid plexus is provided. Compositions and methods of isolating and using the cell also is provided.

21 Claims, 12 Drawing Sheets

(56) References Cited

OTHER PUBLICATIONS

Jeon et al., "Bone marrow mesenchymal stem cells are progenitors in vitro for inner ear hair cells." Mol Cell Neurosci 34: 59-68 (2007).
Johansson et al., "Identification of a neural stem cell in the adult mammalian central nervous system." Cell 96: 25-34 (1999).
Kakigi et al., "Effect of artificial endolymph injection into the cochlear duct on the endocochlear potential." Hear Res 116:113-118 (1998).
Ke et al., "Early response of endogenous adult neural progenitor cells to acute spinal cord injury in mice." Stem Cells 24: 1011-1019 (2006).
Kim et al., "Alteration of E-cadherin and beta-catenin in mouse vestibular epithelia during induction of apoptosis." Neurosci Lett 329: 173-176 (2002).
Knirsch et al, "Persistence of Ca(v)1.3 Ca2+ channels in mature outer hair cells supports outer hair cell afferent signaling." J Neurosci 27: 6442-6451 (2007).
Kozel et al., "Balance and hearing deficits in mice with a null mutation in the gene encoding plasma membrane Ca2+-ATPase isoform 2." J Biol Chem. 273(30):18693-6 (1998).
Kros et al., "Reduced climbing and increased slipping adaptation in cochlear hair cells of mice with Myo7a mutations." Nat Neurosci 5:41-47 (2002).
Laywell et al., "Identification of a multipotent astrocytic stem cell in the immature and adult mouse brain." Proc Natl Acad Sci USA 97: 13883-13888 (2000).
Li et al., "Generation of hair cells by stepwise differentiation of embryonic stem cells." Proc Natl Acad Sci USA 100: 13495-13500 (2003).
Li et al., "Pluripotent stem cells from the adult mouse inner ear." Nat Med 9: 1293-1299 (2003).
Lim et al., "Noggin antagonizes BMP signaling to create a niche for adult neurogenesis." Neuron 28: 713-726 (2000).
Lohmann et al., "Tyrosine phosphatase inhibition induces loss of blood-brain barrier integrity by matrix metalloproteinase-dependent and -independent pathways." Brain Res 995:184-196 (2004).
Martinez-Monedero et al., "Reinnervation of hair cells by auditory neurons after selective removal of spiral ganglion neurons." J Neurobiol 66: 319-331 (2006).
Meyers et al., "Lighting up the senses: FM1-43 loading of sensory cells through nonselective ion channels." J Neurosci 23: 4054-4065 (2003).
Ming et al., "Adult neurogenesis in the mammalian central nervous system." Annu Rev Neurosci 28: 223-250 (2005).
Morshead et al., "The ablation of glial fibrillary acidic protein-positive cells from the adult central nervous system results in the loss of forebrain neural stem cells but not retinal stem cells." Eur J Neurosci 18: 76-84 (2003).
Nakagawa et al., "Cell therapy for inner ear diseases." Curr Pharm Des 11: 1203-1207 (2005).
Nichols et al., "Inward rectifier potassium channels." Annu Rev Physiol 59: 171-191 (1997).
Olivius et al., "Allografted fetal dorsal root ganglion neuronal survival in the guinea pig cochlea." Brain Res 979:1-6 (2003).
Oshima et al., "Differential distribution of stem cells in the auditory and vestibular organs of the inner ear." J Assoc Res Otolaryngol 8: 18-31 (2007).
Regala et al. "Xenografted fetal dorsal root ganglion, embryonic stem cell and adult neural stem cell survival following implantation into the adult vestibulocochlear nerve." Exp Neurol 193: 326-333 (2005).
Roehm et al. "Strategies to preserve or regenerate spiral ganglion neurons." Curr Op in Otolaryngol Head Neck Surg 13: 294-300 (2005).
Sanai et al., "Unique astrocyte ribbon in adult human brain contains neural stem cells but lacks chain migration." Nature 427: 740-744 (2004).
Shihabuddin et al., "Adult spinal cord stem cells generate neurons after transplantation in the adult dentate gyms." J Neurosci 20: 8727-8735 (2000).
Shou et al., "Robust generation of new hair cells in the mature mammalian inner ear by adenoviral expression of Hath1." Mol Cell Neurosci 23: 169-179 (2003).
Si et al., "Developmental assembly of transduction apparatus in chick basilar papilla." J Neurosci 23: 1 10815-10826 (2003).
Song et al., "Neural stem cells from adult hippocampus develop essential properties of functional CNS neurons." Nat Neurosci 5: 438-445 (2002).
Spassky et al., "Adult ependymal cells are postmitotic and are derived from radial glial cells during embryogenesis." J Neurosci 25: 10-18 (2005).
Stankovic et al., "Survival of adult spiral ganglion neurons requires erbB receptor signaling in the inner ear." J Neurosci 24: 8651-8661 (2004).
Strazielle et al., "Pro-inflammatory,cytokines modulate matrix metalloproteinase secretion and organic anion transport at the blood-cerebrospinal fluid barrier." J Neuropathol Exp Neurol 62:1254-1264 (2003).
Vats et al., "Stem cells: sources and applications." Clin Otolaryngol Allied Sci 27:227-232 (2002).
Warchol et al., "Regenerative proliferation in inner ear sensory epithelia from adult guinea pigs and humans." Science 259: 1619-1622 (1993).
Wei et al., "Survival, synaptogenesis, and regeneration of adult mouse spiral ganglion neurons in vitro." Dev Neurobiol 67: 108-122 (2007).
Weil et al., "Defective myosin VIIA gene responsible for Usher syndrome type IB." Nature 374:60-61 (1995).
Yang et al., "Matrix metalloproteinase-mediated disruption of tight junction proteins in cerebral vessels is reversed by synthetic matrix metalloproteinase inhibitor in focal ischemia in rat." J Cereb Blood Flow Metab 27 :697-709 (2007).
Yu et al., "Human Induced Pluripotent Stem Cells Free of Vector and Transgene Sequences," Science, 324:797-801 (2009).
Zecevic, "Specific characteristic of radial glia in the human fetal telencephalon." Glia 48: 27-35 (2004).
Zhang et al., "Stroke induces ependymal cell transformation into radial glia in the subventricular zone of the adult rodent brain." J Cereb Blood Flow Metab 27: 1201-1212 (2007).
Zheng et al., "Immunocytochemical and morphological evidence for intracellular self-repair as an important contributor to mammalian hair cell recovery." J Neurosci 19: 2161-2170 (1999).
Zheng et al., "Overexpression of Math1 induces robust production of extra hair cells in postnatal rat inner ears." Nat Neurosci 3: 580-586 (2000).
Itokazu, Y. et al. (2006) "Choroid Plexus Ependymal Cells Host Neural Progenitor Cells in the Rat," GLIA 53: 32-42.
Wei, D. et al. (2008) "Cells of adult brain germinal zone have properties akin to hair cells and can be used to replace inner ear sensory cells after damage," PNAS 105(52): 21000-21005.

\* cited by examiner

LATERAL VENTRICLE CELL COMPOSITIONS AND USE FOR TREATING NEURAL DEGENERATIVE DISEASES

CROSS-REFERENCE TO THE RELATED APPLICATIONS

This application is a national stage application under 35 U.S.C. §371 of International Application No. PCT/US2009/065758, filed Nov. 24, 2009, which in turn claims the benefit under 35 U.S.C. §119(e) of U.S. Provisional Application Ser. No. 61/118,403, filed Nov. 26, 2008, the contents of each of which is hereby incorporated by reference into the present disclosure.

STATEMENT OF GOVERNMENT SUPPORT

This invention was made with government support under Contract No. DC003826 awarded by The National Institutes of Health. The government has certain rights in the invention.

This invention was also made possible by a grant from the California Institute for Regenerative Medicine ("CIRM" Grant Number RS1-00453-1). The contents of this application are solely the responsibility of the inventors and do not necessarily represent the official views of CIRM or any other agency of the State of California.

BACKGROUND

Throughout and within this application various technical and patent literature are referenced either explicitly or by reference to an Arabic numeral. The bibliographic citations for the Arabic numeral citations is found after the experimental examples. The contents of these technical and patent citations are incorporated by reference into this application to more fully describe the state of the art to which this invention pertains.

Sensorineural hearing loss affects millions of people worldwide. In the mammalian auditory system, hair cells (HCs), the sensory receptor cell to sound and acceleration, are terminally differentiated cells. Degeneration of these cells, due to overstimulation, ototoxic drugs and aging, is the most common cause of hearing loss affecting ~10% of the worldwide population. Since HCs provide survival promoting stimuli (1) to spiral ganglia neurons (SGNs), a secondary effect of HC loss is the gradual degeneration and death of SGNs, leading to structural and electrical remodeling of the cochlear nucleus (CN).

In mammals, this impairment is irreversible due to the incapacity of the cochlea to replace lost HCs. Cell replacement therapy has become an attractive solution for hearing restoration. Recent reports have demonstrated that limited new HCs may be regenerated de novo(2) or via phenotypical trans-differentiation(3, 4) within the adult mammalian inner ear. Moreover, a small number of new SGNs can also be generated from the mature inner ear (5). However, the production of new HCs and SGNs is a rare event. Thus, considerable efforts have been made to identify a renewable cell source able to reconstruct damaged inner ears, with a special focus on various progenitor cells(2, 6-8), albeit limited success.

Thus, there is a need for an effective, reproducible and clinically applicable method to generate functional hair cells. This invention satisfies this need and provides related advantages as well.

SUMMARY OF THE INVENTION

Ten percent of the world's population suffers from hearing loss due to damaged hair cells of the inner ear. Hair cells (HC) regenerate at an extremely low rate. And hair cells supply signals that promote the survival of spiral ganglia neurons (SGNs), the next link in the sonic signaling chain; once the hair cells die, so do the SGNs. Applicants have discovered that there exists a source of replacement cells for both HC and SGNs, in the lateral ventricle or choroid plexus that can serve as biological implants for the deaf and hard of hearing.

Applicants also have discovered both neural stem cells and epithelial cells covered with cilia. The epithelial cells physically and biochemically resemble HC. Applicants have shown that these epithelial cells can form synapses with SGNs and integrate into whole chocleas. The neural stem cells from the lateral ventricle can develop into neurons that function similarly to SGNs and form working synapses.

This invention provides the cell and compositions to accomplish the above therapies. The cell is an isolated ependymal cell that expresses the biochemical marker myosin VIIA. The isolated ependymal cells of this invention were found in the ependymal layer of the lateral ventricle (LV) or the choroid plexus. In a further aspect, the isolated ependymal cell of this invention is further distinguished by expression of one or more of the markers phalloidin, ribeye or myosin VI or the ability to establish synapse-like contact with a spiral ganglia neuron (SGN). The isolated cell of this invention can be yet further distinguished from other cell types because it does not express a glial cell marker, a glial fibrillary acidic protein (GFAP) or a neuronal marker of the group consisting of TuJ1, NeuN, Neurofilament or combinations thereof (isolated from the LV) or the marker Hes1 (isolated from the choroid plexus). In a further aspect, the cells can be distinguished from other cell types by the expression or possession of the markers Pax2, BMP7 and AcHR alpha 9 receptors.

The cells can be genetically modified or cultured to induce differentiation. Alternatively, they can be cultured in a manner to promote clonal replication of the isolated cells. The cells can be modified by attachment of a label or other marker for easy identification. The cells or populations can be combined with a pharmaceutically acceptable or other carrier for therapeutic or diagnostic use.

Methods to isolate the cells and provide the therapeutic or diagnostic uses are further provided herein. The cells can be administered to a subject in need thereof. The cells can be autologous or allogeneic to the subject receiving the treatment.

BRIEF DESCRIPTION OF THE FIGURES

(d, right panel) Similar results could be seen by a HC depolarization of 0.8 nA, leading to a corresponding action potential from a SGN. For SGNs in culture, action potentials could be generated at −50 mV resting potential. Scale bars: a1-a4, b3, c1-c4=20 µm, b1, b2=100 µm

FIG. 12e shows myosin VI, another specific structure protein of inner ear hair cells, also expressed in CP epithelial cells. Accordingly, CP cells take the shape of polarized columnar epithelial cells with enriched stereocilia-like microvilli localized on top of them (12f-i). Expression of additional HC related molecules also have been detected at RNA level (12j) and some of them have been detected at protein level. In addition to the expression of specific hair cell markers, the CP cells were also characterized by the absence of inner-ear supporting cell marker Hes1 (12k).

FIGS. 13a1 and 13a2 show the uptake of FM1-43 in CP epithelial cells. FIGS. 13b1 and 13b2 show that the uptake of FM1-43 was inhibited by dihydrostreptomycin (DHS), an aminoglycoside antibiotics use the same entry pathway in hair cells. FIG. 13c shows that when vibrations was applied with different frequency onto the stereocilia-like structures of CP epithelial cells, the introduced mechanical stimuli evoked similar characteristic electrophysiological response in CP epithelial cells as HCs responded to the sound wave-induced vibration. FIG. 13e shows that CP epithelial cells could blend into the co-cultured cochlear sensory epithelia, where HCs were already picked-off to mimic the primary HC loss. To verify the possibility for the CP epithelial cells to establish functional connections with SGNs, CP was co-cultured with deafferentated SGNs. FIG. 13f shows some of the regenerated neurites recognized CP epithelial cells as their targets and arborized to innervate them. FIG. 13g shows that transmission electron microcopy detected synaptic structure between coupled CP-SGN. The mechanical stimulations exerted on CP epithelial cells elicited corresponding synaptic responses at their coupled SGNs as shown in FIG. 13d. FIG. 13h shows that with reverse transcription-polymerase chain reaction (RT-PCR), active transcription of various neurotrophic factors was detected in CP epithelial cells. FIG. 13i shows that when co-cultured with isolated SGNS, CP epithelial cells demonstrated a significant neural protective effect on SGNs, with comparable level as conferred by synthesized neurotrophic factors.

DETAILED DESCRIPTION OF THE INVENTION

Definitions

Figure 1:
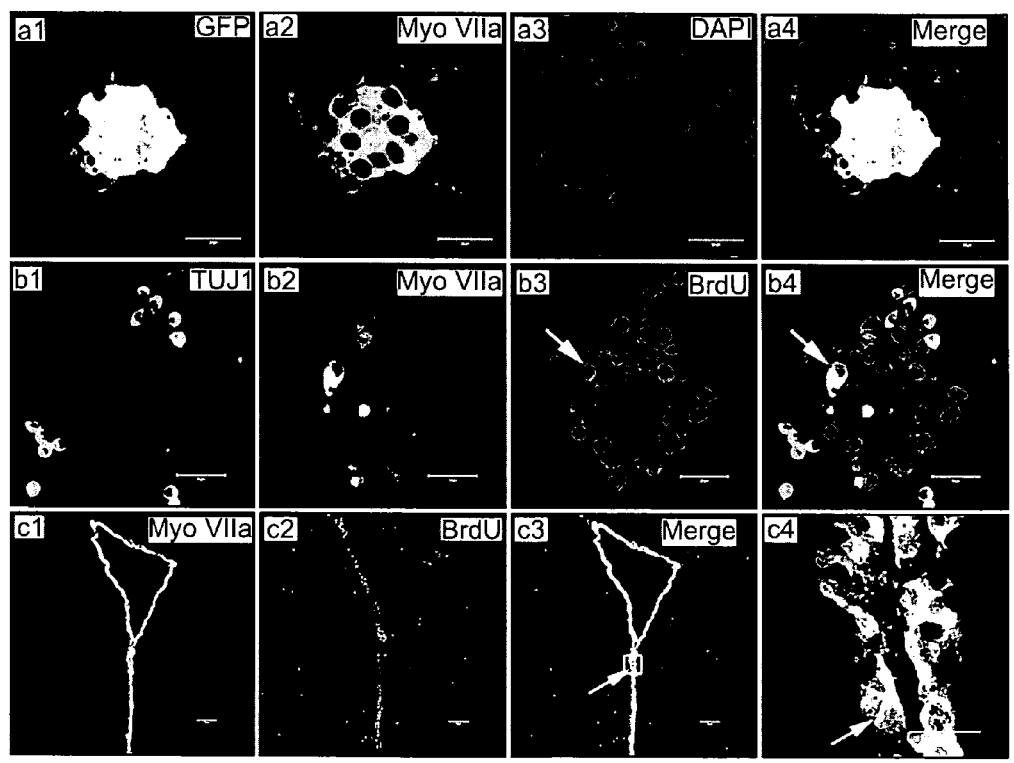
FIG. 1 shows in vivo and in vitro proliferation of ependymal cells. (a1-a4) Adult neural stem cells (NSCs) were isolated from the lateral wall of the lateral ventricle (LV) (obtained from Myosin VIIA-Green Fluorescent Protein (GFP) mice). Dissociated cells proliferated into neurospheres. Within the neurosphere a small cell colony was co-labeled with GFP (a1) and myosin VIIA (a2), indicating the possible proliferation of myosin VIIA positive cells. Nuclei were labeled with (DAPI) (a3, a4) and (b1-b4). After the neurospheres attached to the coverslips, some of the progenies expressed the early neuronal maker β tubulin III (TUJ1), (b1) and myosin VIIA (b2), respectively. Newly generated cells were labeled with bromodeoxyuridine (BrdU). Arrows indicate an in vitro proliferated cell, which was simultaneously labeled with myosin VIIA and BrdU (b3-b4). (c1-c4) Cryosection of an adult brain taken from a BrdU treated mouse. The ependymal layer of the LV was clearly and specifically labeled with myosin VIIA (c1). Nuclei of proliferated cells were labeled with BrdU (c2). Arrows indicate an ependymal cell that was colabeled with myosin VIIA and BrdU. Higher magnification of the co-labeled ependymal cell within the box area can be found in panel (c4), which indicates the possible in vivo proliferation. Scale Bars: a1-b4, c1-c3=100 μm.

The practice of the present invention will employ, unless otherwise indicated, conventional techniques of tissue culture, immunology, molecular biology, microbiology, cell biology and recombinant DNA, which are within the skill of the art. See, e.g., Sambrook, Fritsch and Maniatis, Molecular Cloning: A Laboratory Manual, $2^{nd}$ edition (1989); Current Protocols In Molecular Biology (F. M. Ausubel, et al. eds., (1987)); the series Methods in Enzymology (Academic Press, Inc.): PCR 2: A Practical Approach (M. J. MacPherson, B. D. Hames and G. R. Taylor eds. (1995)); Harlow and Lane, eds. (1988) Antibodies, A Laboratory Manual; Harlow and Lane, eds. (1999) Using Antibodies, A Laboratory Manual; Animal Cell Culture (R. I. Freshney, ed. (1987)); Zigova, Sanberg and Sanchez-Ramos, eds. (2002) Neural Stem Cells.

All numerical designations, e.g., pH, temperature, time, concentration, and molecular weight, including ranges, are approximations which are varied (+) or (−) by increments of 1.0 or 0.1, as appropriate. It is to be understood, although not always explicitly stated that all numerical designations are preceded by the term "about". It also is to be understood, although not always explicitly stated, that the reagents described herein are merely exemplary and that equivalents of such are known in the art.

As used in the specification and claims, the singular form "a", "an" and "the" include plural references unless the context clearly dictates otherwise. For example, the term "a cell" includes a plurality of cells, including mixtures thereof.

As used herein, the term "comprising" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions of this invention or process steps to produce a composition or achieve an intended result. Embodiments defined by each of these transition terms are within the scope of this invention.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polymer. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

A "gene" refers to a polynucleotide containing at least one open reading frame (ORF) that is capable of encoding a particular polypeptide or protein after being transcribed and translated. Any of the polynucleotide sequences described herein may be used to identify larger fragments or full-length coding sequences of the gene with which they are associated. Methods of isolating larger fragment sequences are known to those of skill in the art.

The term "express" refers to the production of a gene product.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in an eukaryotic cell. "Differentially expressed" as applied to a gene, refers to the differential production of the mRNA transcribed from the gene or the protein product encoded by the gene. A differentially expressed gene may be overexpressed or underexpressed as compared to the expression level of a normal or control cell. In one aspect, it refers to overexpression that is 1.5 times, or alternatively, 2 times, or alternatively, at least 2.5 times, or alternatively, at least 3.0 times, or alternatively, at least 3.5 times, or alternatively, at least 4.0 times, or alternatively, at least 5 times, or alternatively 10 times higher (i.e., and therefore overexpressed) or lower than the expression level detected in a control sample. The term "differentially expressed" also refers to nucleotide sequences in a cell or tissue which are expressed where silent in a control cell or not expressed where expressed in a control cell.

A "gene product" or alternatively a "gene expression product" refers to the amino acid (e.g., peptide or polypeptide) generated when a gene is transcribed and translated.

"Under transcriptional control" is a term well understood in the art and indicates that transcription of a polynucleotide sequence, usually a DNA sequence, depends on its being operatively linked to an element which contributes to the initiation of, or promotes, transcription. "Operatively linked" intends the polynucleotides are arranged in a manner that allows them to function in a cell.

A "gene delivery vehicle" is defined as any molecule that can carry inserted polynucleotides into a host cell. Examples of gene delivery vehicles are liposomes, biocompatible polymers, including natural polymers and synthetic polymers; lipoproteins; polypeptides; polysaccharides; lipopolysaccharides; artificial viral envelopes; metal particles; and bacteria, or viruses, such as baculovirus, adenovirus and retrovirus, bacteriophage, cosmid, plasmid, fungal vectors and other recombination vehicles typically used in the art which have been described for expression in a variety of eukaryotic and prokaryotic hosts, and may be used for gene therapy as well as for simple protein expression.

"Gene delivery," "gene transfer," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art and described herein.

A "viral vector" is defined as a recombinantly produced virus or viral particle that comprises a polynucleotide to be delivered into a host cell, either in vivo, ex vivo or in vitro. Examples of viral vectors include retroviral vectors, adenovirus vectors, adeno-associated virus vectors, alphavirus vectors and the like. Alphavirus vectors, such as Semliki Forest virus-based vectors and Sindbis virus-based vectors, have also been developed for use in gene therapy and immunotherapy. See, Schlesinger and Dubensky (1999) Curr. Opin. Biotechnol. 5:434-439 and Ying, et al. (1999) Nat. Med. 5(7):823-827. In aspects where gene transfer is mediated by a retroviral vector, a vector construct refers to the polynucleotide comprising the retroviral genome or part thereof, and a therapeutic gene. As used herein, "retroviral mediated gene transfer" or "retroviral transduction" carries the same meaning and refers to the process by which a gene or nucleic acid sequences are stably transferred into the host cell by virtue of the virus entering the cell and integrating its genome into the host cell genome. The virus can enter the host cell via its normal mechanism of infection or be modified such that it binds to a different host cell surface receptor or ligand to enter the cell. As used herein, retroviral vector refers to a viral particle capable of introducing exogenous nucleic acid into a cell through a viral or viral-like entry mechanism.

Retroviruses carry their genetic information in the form of RNA; however, once the virus infects a cell, the RNA is reverse-transcribed into the DNA form which integrates into the genomic DNA of the infected cell. The integrated DNA form is called a provirus.

In aspects where gene transfer is mediated by a DNA viral vector, such as an adenovirus (Ad) or adeno-associated virus (AAV), a vector construct refers to the polynucleotide comprising the viral genome or part thereof, and a transgene. Adenoviruses (Ads) are a relatively well characterized, homogenous group of viruses, including over 50 serotypes. See, e.g., International PCT Application No. WO 95/27071. Ads do not require integration into the host cell genome. Recombinant Ad derived vectors, particularly those that reduce the potential for recombination and generation of wild-type virus, have also been constructed. See, International PCT Application Nos. WO 95/00655 and WO 95/11984. Wild-type AAV has high infectivity and specificity integrating into the host cell's genome. See, Hermonat and Muzyczka (1984) Proc. Natl. Acad. Sci. USA 81:6466-6470 and Lebkowski, et al. (1988) Mol. Cell. Biol. 8:3988-3996.

Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression.

Gene delivery vehicles also include several non-viral vectors, including DNA/liposome complexes, and targeted viral protein-DNA complexes. Liposomes that also comprise a targeting antibody or fragment thereof can be used in the methods of this invention. To enhance delivery to a cell, the nucleic acid or proteins of this invention can be conjugated to antibodies or binding fragments thereof which bind cell surface antigens, e.g., a cell surface marker found on stem cells.

A "probe" when used in the context of polynucleotide manipulation refers to an oligonucleotide that is provided as a reagent to detect a target potentially present in a sample of interest by hybridizing with the target. Usually, a probe will comprise a label or a means by which a label can be attached, either before or subsequent to the hybridization reaction. Suitable labels include, but are not limited to radioisotopes, fluorochromes, chemiluminescent compounds, dyes, and proteins, including enzymes.

A "primer" is a short polynucleotide, generally with a free 3'-OH group that binds to a target or "template" potentially present in a sample of interest by hybridizing with the target, and thereafter promoting polymerization of a polynucleotide complementary to the target. A "polymerase chain reaction" ("PCR") is a reaction in which replicate copies are made of a target polynucleotide using a "pair of primers" or a "set of primers" consisting of an "upstream" and a "downstream" primer, and a catalyst of polymerization, such as a DNA polymerase, and typically a thermally-stable polymerase enzyme. Methods for PCR are well known in the art, and taught, for example in "PCR: A Practical Approach" (M. MacPherson et al., IRL Press at Oxford University Press (1991)). All processes of producing replicate copies of a polynucleotide, such as PCR or gene cloning, are collectively referred to herein as "replication." A primer can also be used as a probe in hybridization reactions, such as Southern or Northern blot analyses. Sambrook et al., infra.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Hybridization reactions can be performed under conditions of different "stringency". In general, a low stringency hybridization reaction is carried out at about 40° C. in 10×SSC or a solution of equivalent ionic strength/temperature. A moderate stringency hybridization is typically performed at about 50° C. in 6×SSC, and a high stringency hybridization reaction is generally performed at about 60° C. in 1×SSC.

When hybridization occurs in an antiparallel configuration between two single-stranded polynucleotides, the reaction is called "annealing" and those polynucleotides are described as "complementary". A double-stranded polynucleotide can be "complementary" or "homologous" to another polynucleotide, if hybridization can occur between one of the strands of the first polynucleotide and the second. "Complementarity" or "homology" (the degree that one polynucleotide is complementary with another) is quantifiable in terms of the proportion of bases in opposing strands that are expected to form hydrogen bonding with each other, according to generally accepted base-pairing rules.

A polynucleotide or polynucleotide region (or a polypeptide or polypeptide region) has a certain percentage (for example, 80%, 85%, 90%, or 95%) of "sequence identity" to another sequence means that, when aligned, that percentage of bases (or amino acids) are the same in comparing the two sequences. This alignment and the percent homology or sequence identity can be determined using software programs known in the art, for example those described in Current Protocols in Molecular Biology (F. M. Ausubel et al., eds., 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwisProtein+SPupdate+PIR. Details of these programs can be found at the following Internet address: http://www.ncbi.nlm.nih.gov/cgi-bin/BLAST.

The term "polypeptide" is used interchangeably with the term "protein" and in its broadest sense refers to a compound of two or more subunit amino acids, amino acid analogs or peptidomimetics. The subunits may be linked by peptide bonds. In another embodiment, the subunit may be linked by other bonds, e.g., ester, ether, etc. As used herein the term "amino acid" refers to either natural and/or unnatural or synthetic amino acids, including glycine and both the D and L optical isomers, amino acid analogs and peptidomimetics. A peptide of three or more amino acids is commonly called an oligopeptide if the peptide chain is short. If the peptide chain is long, the peptide is commonly called a polypeptide or a protein.

"Under transcriptional control" is a term well understood in the art and indicates that transcription of a polynucleotide sequence, usually a DNA sequence, depends on its being operatively linked to an element which contributes to the initiation of, or promotes, transcription. "Operatively linked" refers to a juxtaposition wherein the elements are in an arrangement allowing them to function.

A "composition" is intended to mean a combination of active agent, cell or population of cells and another compound or composition, inert (for example, a detectable agent or label or biocompatible scaffold) or active, such as a growth and/or differentiation factor.

"Substantially homogeneous" describes a population of cells in which more than about 50%, or alternatively more than about 60%, or alternatively more than 70%, or alternatively more than 75%, or alternatively more than 80%, or alternatively more than 85%, or alternatively more than 90%, or alternatively, more than 95%, of the cells are of the same or similar phenotype. Phenotype can be determined by a pre-selected cell surface marker or other marker, e.g. myosin or actin or the expression of a gene or protein, e.g. a calcium handling protein, a t-tubule protein or alternatively, a calcium pump protein. In another aspects, the substantially homogenous population have a decreased (e.g., less than about 95%, or alternatively less than about 90%, or alternatively less than about 80%, or alternatively less than about 75%, or alternatively less than about 70%, or alternatively less than about 65%, or alternatively less than about 60%, or alternatively less than about 55%, or alternatively less than about 50%) of the normal level of expression than the wild-type counterpart cell or tissue.

A "pharmaceutical composition" is intended to include the combination of an active agent with a carrier, inert or active such as a biocompatible scaffold, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin, Remington's Pharm. Sci., 15th Ed. (Mack Publ. Co., Easton (1975)). The term includes carriers that facilitate controlled release of the active agent as well as immediate release.

For topical use, the pharmaceutically acceptable carrier is suitable for manufacture of creams, ointments, jellies, gels, solutions, suspensions, etc. Such carriers are conventional in the art, e.g., for topical administration with polyethylene glycol (PEG). These formulations may optionally comprise additional pharmaceutically acceptable ingredients such as diluents, stabilizers, and/or adjuvants.

A "subject" of diagnosis or treatment is a cell or a mammal, including a human. Non-human animals subject to diagnosis or treatment include, for example, simians, murines, guinea pigs, canines, such as dogs, leporids, such as rabbits, livestock, such as bovine or porcine, sport animals, and pets.

An "effective amount" is an amount sufficient to effect beneficial or desired results. An effective amount can be administered in one or more administrations, applications or dosages and can be empirically determined by those of skill in the art.

A "control" is an alternative subject or sample used in an experiment for comparison purpose. A control can be "positive" or "negative". For example, where the purpose of the experiment is to determine a correlation of an altered expression level of a gene with a particular phenotype, it is generally preferable to use a positive control (a sample from a subject, carrying such alteration and exhibiting the desired phenotype), and a negative control (a subject or a sample from a subject lacking the altered expression or phenotype).

As used herein, the terms "treating," "treatment" and the like are used herein to mean obtaining a desired pharmacologic and/or physiologic effect. The effect can be prophylactic in terms of completely or partially preventing a disorder or sign or symptom thereof, and/or can be therapeutic in terms of a partial or complete cure for a disorder and/or adverse effect attributable to the disorder. Examples of "treatment" include but are not limited to: preventing a disorder from occurring in a subject that may be predisposed to a disorder, but has not yet been diagnosed as having it; inhibiting a disorder, i.e., arresting its development; and/or relieving or ameliorating the symptoms of disorder, e.g., hearing loss. As is understood by those skilled in the art, "treatment" can include systemic amelioration of the symptoms associated with the pathology and/or a delay in onset of symptoms such as loss of hearing.

The term "isolated" or "purified" means separated from constituents, cellular and otherwise, in which the cell, tissue, polynucleotide, peptide, polypeptide, protein, antibody or fragment(s) thereof, which are normally associated in nature. For example, an isolated polynucleotide is separated from the 3' and 5' contiguous nucleotides with which it is normally associated in its native or natural environment, e.g., on the chromosome. As is apparent to those of skill in the art, a non-naturally occurring polynucleotide, peptide, polypeptide, protein, antibody or fragment(s) thereof, does not require "isolation" to distinguish it from its naturally occurring counterpart. An isolated cell is a cell that is separated form tissue or cells of dissimilar phenotype or genotype.

As used herein, "stem cell" defines a cell with the ability to divide for indefinite periods in culture and give rise to specialized cells. At this time and for convenience, stem cells are categorized as somatic (adult) or embryonic. A somatic stem cell is an undifferentiated cell found in a differentiated tissue that can renew itself (clonal) and (with certain limitations) differentiate to yield all the specialized cell types of the tissue from which it originated. An embryonic stem cell is a primitive (undifferentiated) cell from the embryo that has the potential to become a wide variety of specialized cell types. An embryonic stem cell is one that has been cultured under in vitro conditions that allow proliferation without differentiation for months to years. Non-limiting examples of embryonic stem cells are the HES2 (also known as ES02) cell line available from ESI, Singapore and the H1 (also know as WA01) cell line available from WiCells, Madison, Wis. Pluripotent embryonic stem cells can be distinguished from other types of cells by the use of marker including, but not limited to, Oct-4, alkaline phosphatase, CD30, TDGF-1, GCTM-2, Genesis, Germ cell nuclear factor, SSEA1, SSEA3, and SSEA4.

A "neural or neuronal stem cell" as used herein refers to a cell that has the ability to self-replicate and give rise to multiple specialized cell types of the nervous system. In some aspect, a neural stem cell is a multipotential neural stem cell in the subventricular zone (SVZ) of the forebrain lateral ventricle (LV).

A clone or "clonal population" is a line of cells that is genetically identical to the originating cell; in this case, a stem cell. A "precursor" or "progenitor cell" intends to mean cells that have a capacity to differentiate into a specific type of cell. A progenitor cell may be a stem cell. A progenitor cell may also be more specific than a stem cell. A progenitor cell may be unipotent or multipotent. Compared to adult stem cells, a progenitor cell may be in a farther stage of cell differentiation. Progenitor cells are often found in adult organisms, they act as a repair system for the body. Examples of progenitor cells include, but are not limited to, satellite cells found in muscles, intermediate progenitor cells formed in the subventricular zone, bone marrow stromal cells, periosteum progenitor cells, pancreatic progenitor cells and angioblasts or endothelial progenitor cells. Examples of progenitor cells may also include, but are not limited to, an ependymal cell and a neural stem cell from the forebrain lateral ventricle (LV).

The term "propagate" means to grow or alter the phenotype of a cell or population of cells. The term "growing" refers to the proliferation of cells in the presence of supporting media, nutrients, growth factors, support cells, or any chemical or biological compound necessary for obtaining the desired number of cells or cell type. In one embodiment, the growing of cells results in the regeneration of tissue.

The term "culturing" refers to the in vitro propagation of cells or organisms on or in media of various kinds. It is understood that the descendants of a cell grown in culture may not be completely identical (i.e., morphologically, genetically, or phenotypically) to the parent cell. By "expanded" is meant any proliferation or division of cells.

"Clonal proliferation" refers to the growth of a population of cells by the continuous division of single cells into two identical daughter cells and/or population of identical cells.

As used herein, the "lineage" of a cell defines the heredity of the cell, i.e. its predecessors and progeny. The lineage of a cell places the cell within a hereditary scheme of development and differentiation.

A derivative of a cell or population of cells is a daughter cell of the isolated cell or population of cells. Derivatives include the expanded clonal cells or differentiated cells cultured and propagated from the isolated stem cell or population of stem cells. Derivatives also include already derived stem cells or population of stem cells.

"Differentiation" describes the process whereby an unspecialized cell acquires the features of a specialized cell such as a heart, liver, or muscle cell. "Directed differentiation" refers to the manipulation of stem cell culture conditions to induce differentiation into a particular cell type. "Dedifferentiated" defines a cell that reverts to a less committed position within the lineage of a cell. As used herein, the term "differentiates or differentiated" defines a cell that takes on a more committed ("differentiated") position within the lineage of a cell. As used herein, "a cell that differentiates into a mesodermal (or ectodermal or endodermal) lineage" defines a cell that becomes committed to a specific mesodermal, ectodermal or endodermal lineage, respectively. Examples of cells that differentiate into a mesodermal lineage or give rise to specific mesodermal cells include, but are not limited to, cells that are adipogenic, leiomyogenic, chondrogenic, cardiogenic, dermatogenic, hematopoetic, hemangiogenic, myogenic, nephrogenic, urogenitogenic, osteogenic, pericardiogenic, or stromal.

Examples of cells that differentiate into ectodermal lineage include, but are not limited to epidermal cells, neurogenic cells, and neurogliagenic cells.

Examples of cells that differentiate into endodermal lineage include, but are not limited to pleurogenic cells, and hepatogenic cells, cell that give rise to the lining of the intestine, and cells that give rise to pancreogenic and splanchogenic cells.

As used herein, a "pluripotent cell" defines a less differentiated cell that can give rise to at least two distinct (genotypically and/or phenotypically) further differentiated progeny cells. In another aspect, a "pluripotent cell" includes a Induced Pluripotent Stem Cell (iPSC) which is an artificially derived stem cell from a non-pluripotent cell, typically an adult somatic cell, produced by inducing expression of one or more stem cell specific genes. Such stem cell specific genes include, but are not limited to, the family of octamer transcription factors, i.e. Oct-3/4; the family of Sox genes, i.e. Sox1, Sox2, Sox3, Sox 15 and Sox 18; the family of Klf genes, i.e. Klf1, Klf2, Klf4 and Klf5; the family of Myc genes, i.e. c-myc and L-myc; the family of Nanog genes, i.e. OCT4, NANOG and REX1; or LIN28. Examples of iPSCs are described in Takahashi K. et al. (2007) Cell advance online publication 20 Nov. 2007; Takahashi K. & Yamanaka S. (2006) Cell 126: 663-76; Okita K. et al. (2007) Nature 448: 260-262; Yu, J. et al. (2007) Science advance online publication 20 Nov. 2007; and Nakagawa, M. et al. (2007) Nat. Biotechnol. Advance online publication 30 Nov. 2007.

A "multi-lineage stem cell" or "multipotent stem cell" refers to a stem cell that reproduces itself and at least two further differentiated progeny cells from distinct developmental lineages. The lineages can be from the same germ layer (i.e. mesoderm, ectoderm or endoderm), or from different germ layers. An example of two progeny cells with distinct developmental lineages from differentiation of a multi-lineage stem cell is a myogenic cell and an adipogenic cell (both are of mesodermal origin, yet give rise to different tissues). Another example is a neurogenic cell (of ectodermal origin) and adipogenic cell (of mesodermal origin).

A neural stem cell is a cell that can be isolated from the adult central nervous systems of mammals, including humans. They have been shown to generate neurons, migrate and send out aconal and dendritic projections and integrate into pre-existing neuroal circuits and contribute to normal brain function. Reviews of research in this area are found in Miller (2006) The Promise of Stem Cells for Neural Repair, Brain Res. Vol. 1091(1):258-264; Pluchino et al. (2005) Neural Stem Cells and Their Use as Therapeutic Tool in Neurological Disorders, Brain Res. Brain Res. Rev., Vol. 48(2):211-219; and Goh, et al. (2003) Adult Neural Stem Cells and Repair of the Adult Central Nervous System, J. Hematother. Stem Cell Res., Vol. 12(6):671-679.

An "NSC-derived neuron" is a neuron that has been differentiated from an isolated neural stem cell (NSC) or pluripotent cell. In some aspects, the NSC is a multipotential neural stem cell of active neurogenesis located in the subventricular zone (SVZ) beneath the ependymal layer of the forebrain lateral ventricle (LV) region. In some other aspects, the NSC is an isolated multipotential neural stem cell of active neurogenesis from the subventricular zone (SVZ) beneath the ependymal layer of the forebrain lateral ventricle (LV) region. In some embodiments, an NSC is induced to differentiate into the NSC-derived neuron by contacting a hair cell (HC) or a spiral ganglia-like neuron (SGN). In some embodiments, the induction can be facilitated by addition of agents promoting neural cell differentiation and/or growth. In some embodiments, an NSC-derived neuron express synapsin 1 at the nerve ending. In yet some other embodiments, an NSC-derived neuron can establish synaptic contact with a HC or SGN.

A spiral ganglia-like neuron is a neuron in the spiral ganglion which is the group of nerve cells that serve the sense of hearing by sending a representation of sound from the cochlea to the brain. The cell bodies of the spiral ganglion neurons are found in the spiral structure of the cochlea.

The choroid plexus (CP) intends the area on the ventricles of the brain where cerebrospinal fluid (CSF) is produced by modified ependymal cells. Choroid plexus is present in all components of the ventricular system except for the cerebral aqueduct and the occipital and frontal horns of the lateral ventricles. It is found in the superior part of the inferior horn of the lateral ventricles. It follows up along this boundary, continuous with the inferior of the body of the lateral ventricles. It passes into the interventricular foramen, and is present at the top of the third ventricle.

A population of cells intends a collection of more than one cell that is identical (clonal) or non-identical in phenotype and/or genotype.

An ependymal cell is one of four types of neuroglial in the central nervous system (CNS) that functions at least in part in the production of cerebrospinal fluid. Ependymal cells give rise to a rapidly proliferating cells that generate neurons. See Johansson et al. (1999) Cell 96(1):25-34.

A "polarized ependymal cell" refers to an ependymal cell in which the cell membrane is specialized at each region of the cell.

A "ciliate epithelial cell" intends to mean an epithelial cell at the epithelial surface containing tiny hair-like structures beating in synchrony to move secretions or objects around. Non-limiting examples include ciliated epithelia in the vescicles of the brain which circulate the cerebrospinal fluid, and in the oviduct which move the ova from the ovary to the uterus.

"Glial cell marker" refers to a marker specifically present in glial cells but not in cell types like epithelia cells. Glial cells, as used herein, are also referred to as neuroglia or simply glia, which are non-neuronal cells that provide support and nutrition, maintain homeostasis, form myelin, and participate in signal transmission in the nervous system. Examples of glial cell markers include, but are not limited to, glial fibrillary acidic protein (GFAP).

"Glial fibrillary acidic protein" (GFAP) is a major intermediate filament protein of mature astrocytes. It is used as a marker to distinguish astrocytes from other glial cells during development. Mutations in this gene cause Alexander disease, a rare disorder of astrocytes in the central nervous system. Representative sequences of GFAP include UniProt: P14136 and Entrez Gene: 2670, last accessed on Nov. 26, 2008.

"TuJ1" refers to Tubulin beta-III, the major constituent of microtubules. It binds two moles of GTP, one at an exchangeable site on the beta chain and one at a non-exchangeable site on the alpha-chain. Representative sequences of TuJ1 include UniProt: Q13509 and Entrez Gene: 10381, last accessed on Nov. 26, 2008.

"NeuN" is a vertebrate nervous system- and neuron-specific nuclear protein that is also referred to as Neuronal Nuclei. More detailed descriptions can be found in Mullen et al. (1992) Development. 116(1):201-11, incorporated herein in its entirety.

"Neurofilament (NEFH)" usually contains three intermediate filament proteins: L, M, and H which are involved in the maintenance of neuronal caliber. Representative sequences of neurofilament include UniProt: P12036 and Entrez Gene: 4744, last accessed on Nov. 26, 2008.

"Phalloidin" is a toxin that binds specifically to F-actin, which is extensively expressed by the stereocilia of hair cells. More detailed description of phalloidin is found in Hasson et al. (1997) J Cell Biol. 137:1287-1307.

"Ribeye" is described in Schmitz et al. (2000) Neuron 28(3):857-72.

"Myosin VIIa" encodes a protein that is a member of the myosin superfamily of actin-based motors. The myosin VIIa gene was identified as the gene defective in shaker-1, a recessive deafness in mice. Gibson, F., et al. (1995) Nature 374: 62-64, and in human Usher syndrome type 1B, an inherited disease characterized by congenital deafness, vestibular dysfunction, and retinitis pigmentosa. Weil, D. (1995) Nature (London) 374: 60-61. Representative sequences include GenBank Accession Nos. AAC50722.1, AAC50927.1 (*homo sapiens*) and NP_032689.2 (*mus musculus*), last accessed on Nov. 19, 2009. Antibodies to myosin VII are commercially available from Santa Cruz Biotechnology and Abcam, for example.

"Myosin VI" encodes a protein involved intracellular vesicle and organelle transport, especially in the hair cell of the inner ear. Mutations in this gene have been found in patients with non-syndromic autosomal dominant and recessive hearing loss. Representative sequences include UniProt: Q9UM54 and Entrez Gene: 4646, last accessed on Nov. 26, 2008.

"Math1" or "Helix-loop-helix protein hATH-1" belongs to the basic helix-loop-helix (BHLH) family of transcription factors. It activates E-box dependent transcription along with E47. Representative sequences include UniProt: Q92858 and Entrez Gene: 474, last accessed on Nov. 26, 2008.

"Whirlin", or "deafness, autosomal recessive 31" is also referred to as deafness, autosomal recessive 31. Representative sequences include UniProt: Q9P202 and Entrez Gene: 25861, last accessed on Nov. 26, 2008.

"Espin", "Espn" or "deafness, autosomal recessive 36" is a multifunctional actin-bundling protein and it plays a major role in regulating the organization, dimensions, dynamics and signaling capacities of the actin filament-rich, microvillus-type specializations that mediate sensory transduction in various mechanosensory and chemosensory cells. Representative sequences include UniProt: B1AK53 and Entrez Gene: 83715, last accessed on Nov. 26, 2008.

"Tip link", "PCDH15", "protocadherin-15" or "deafness, autosomal recessive 23" is a member of the cadherin superfamily. Family members encode integral membrane proteins that mediate calcium-dependent cell-cell adhesion. The protein product of this gene consists of a signal peptide, 11 extracellular calcium-binding domains, a transmembrane domain and a unique cytoplasmic domain. It plays an essential role in maintenance of normal retinal and cochlear function. Mutations in this gene have been associated with hearing loss, which is consistent with its location at the Usher syndrome type 1F (USH1F) critical region on chromosome 10. Representative sequences include UniProt: Q96QU1 and Entrez Gene: 65217, last accessed on Nov. 26, 2008.

"Hes1" or "hairy and enhancer of split 1" belongs to the basic helix-loop-helix family of transcription factors. It is a transcriptional repressor of genes that require a bHLH protein for their transcription. The protein has a particular type of basic domain that contains a helix interrupting protein that binds to the N-box rather than the canonical E-box. Representative sequences include UniProt: P30042 and Entrez Gene: 3280, last accessed on Nov. 26, 2008.

"Synapsin 1" is a member of the synapsin gene family. Synapsins encode neuronal phosphoproteins which associate with the cytoplasmic surface of synaptic vesicles. Family members are characterized by common protein domains, and they are implicated in synaptogenesis and the modulation of neurotransmitter release, suggesting a potential role in several neuropsychiatric diseases. This member of the synapsin family plays a role in regulation of axonogenesis and synaptogenesis. The protein encoded serves as a substrate for several different protein kinases and phosphorylation may function in the regulation of this protein in the nerve terminal. Mutations in this gene may be associated with X-linked disorders with primary neuronal degeneration such as Rett syndrome. Representative sequences include UniProt: P17600 and Entrez Gene: 6853, last accessed on Nov. 26, 2008.

"Brn 3c" or "Brain-specific homeobox/POU domain protein 3C" may play a role in determining or maintaining the identities of a small subset of visual. Representative sequences include UniProt: Q15319 and Entrez Gene: 5459, last accessed on Nov. 26, 2008.

"Prestin" or "deafness, neurosensory, autosomal recessive, 61" is a member of the SLC26A/Su1P transporter family. It encodes a protein that is specifically expressed in outer hair cells (OHCs) of the cochlea and is essential in auditory processing. Intracellular anions are thought to act as extrinsic voltage sensors, which bind to this protein and trigger the conformational changes required for rapid length changes in OHCs. Mutations in this gene have been associated with non-syndromic hearing loss. Representative sequences include UniProt: P58743 and Entrez Gene: 375611, last accessed on Nov. 26, 2008.

"Otoferlin" or "Fer-1-like protein 2" may be involved in vesicle membranefusion. Representative sequences include UniProt: Q9HC10 and Entrez Gene: 9381, last accessed on Nov. 26, 2008.

"CtBP2" or "C-terminal binding protein 2" produces alternative transcripts encoding two distinct proteins. One protein is a transcriptional repressor, while the other isoform is a major component of specialized synapses known as synaptic ribbons. Both proteins contain a NAD+ binding domain similar to NAD+-dependent 2-hydroxyacid dehydrogenases. Representative sequences include UniProt: P56545 and Entrez Gene: 1488, last accessed on Nov. 26, 2008.

"Myo7a" or "myosin VIIA" is a member of the myosin gene family. Myosins are mechanochemical proteins characterized by the presence of a motor domain, an actin-binding domain, a neck domain that interacts with other proteins, and a tail domain that serves as an anchor. This gene encodes an unconventional myosin with a very short tail. Defects in this gene are associated with the mouse shaker-1 phenotype and the human Usher syndrome 1B which are characterized by deafness, reduced vestibular function, and (in human) retinal degeneration. Representative sequences include UniProt: □13402 and Entrez Gene: 4647, last accessed on Nov. 19, 2009.

"Myo6" or "myosin VI" encodes a protein involved intracellular vesicle and organelle transport, especially in the hair cell of the inner ear. Mutations in this gene have been found in patients with non-syndromic autosomal dominant and recessive hearing loss. Representative sequences include UniProt: Q9UM54 and Entrez Gene: 7605, last accessed on Nov. 19, 2009.

"Hair cells" refer to the sensory receptors of both the auditory system and the vestibular system in all vertebrates. In mammals, the auditory hair cells are located within the organ of Corti on a thin basilar membrane in the cochlea of the inner ear. They derive their name from the tufts of stereocilia that protrude from the apical surface of the cell, a structure known as the hair bundle, into the scala media, a fluid-filled tube within the cochlea. Mammalian cochlear hair cells come in two anatomically and functionally distinct types: the outer and inner hair cells. Damage to these hair cells results in decreased hearing sensitivity, i.e. sensorineural hearing loss.

"Spinal ganglia neuron" or "dorsal root ganglion neuron" is a neuron in the ganglion at the posterior root of each spinal segmental nerve. A spinal ganglion contains the cell bodies of the unipolar primary sensory neurons.

A "neurodegenerative disease" is a condition in which cells of the brain and spinal cord are lost. The brain and spinal cord are composed of neurons that do different functions such as controlling movements, processing sensory information, and making decisions. Cells of the brain and spinal cord are not readily regenerated en masse, so excessive damage can be devastating. Neurodegenerative diseases result from deterioration of neurons or their myelin sheath which over time will lead to dysfunction and disabilities resulting from this. Examples of neurodegenerative diseases include, but are not limited to, sensorineural hearing loss, neonatal and progressive hearing loss, drug-induced hearing loss, noise-induced hearing loss, traumatic inner ear diseases and vestibular disorder related to inner ear disorders.

MODES FOR CARRYING OUT THE INVENTION

Cells, Compositions and Animal Models

This invention provides an isolated ependymal cell that expresses the biochemical marker myosin VIIA. The isolated ependymal cells of this invention were found in the ependymal layer of the lateral ventricle (LV) or the choroid plexus (CP). In the LV there is a germinal zone that produces ciliated epithelial cells.

In a further aspect, the isolated ependymal cell of this invention is further distinguished by expression of one or more of the markers phalloidin, ribeye or myosin VI or the ability to establish synapse-like contact with a spiral ganglia neuron (SGN). The isolated cell of this invention can be yet further distinguished from other cell types because it does not express a glial cell marker, a glial fibrillary acidic protein (GFAP) or a neuronal marker of the group consisting of TuJ1, NeuN, Neurofilament or combinations thereof (isolated from the LV) or the markers Hes1, Myo7A, Myo6, Espn, Brn3c and Ctbp2 (isolated from the choroid plexus). In a further aspect, the cells can be distinguished from other cell types by the expression or possession of the markers Pax2, BMP7 and AcHR alpha 9 receptors. See, Li et al. (2004) Trends in Mol. Med. 10(7):309-315. The cells are columnar is shape and possess the ability to take the shape of polarized epithelial cells. These biochemical and phenotypical characteristics show that the cell is neither a neuron nor a glial cell, but rather a distinct epithelial cell type.

Confirmation of the cell type can be accomplished using visual analysis, immunohistochemical techniques (e.g., antibody staining) or molecular techniques such as the polymerase chain reaction (PCR), using the primer sequences known in the art. By way of example only, a coding sequence for myosin VIIA is provided herein as well as primer sequences.

The cell can be isolated from any suitable subject that includes but is not limited to an animal or mammal such as simians, murines, guinea pigs, canines, such as dogs, leporids, such as rabbits, livestock, such as bovine or porcine, sport animals, and pets, using immunohistochemical techniques known in the art and describe in Wei, (5), incorporated by reference into this application in its entirety.

This invention also provides a population of cells of this invention. In one aspect, the population of cells is a clonal population. In another aspect, the population of cells is a substantially homogeneous population of isolated ependymal cells as described above. In a yet further aspect, the population of cells is one which has been expanded and differentiated from the cell or cells of this invention.

This invention further provides an isolated cell as described above that has been modified by the insertion of any one or more of a label (such as a detectable label, e.g., GFP), an exogenous polynucleotide such as a regulatory unit or open reading frame of a protein. Methods of inserting such compositions are well known in the art, e.g., by the use of insertion and/or expression vectors.

This invention also provides a population of modified cells as described above or yet further, a substantially homogeneous population of ependymal cells that have been modified as described above.

This invention also provides a population of modified cells of this invention. In one aspect, the population of modified cells is a clonal population. In another aspect, the population of modified cells is a substantially homogeneous population of isolated modified ependymal cells as described above. In a yet further aspect, the population of modified cells is one which has been expanded and differentiated from the modified cell or cells of this invention.

Further provided by this invention are any one or more combinations of the above-noted independent modifications. Thus, Applicants' invention includes any one or more combination of the independently described modifications. The preferred modification or combination of modifications will be determined by the use of the modified cells and in some aspects, the patient to be treated with the modified cell or population of cells.

Any of these population of cells can further comprise, or alternatively consist essentially of, or yet further consist of, a neural stem cell (NSC) or a NSC-derived neuron. In one aspect, this cell is an isolated NSC or isolated NSC-derived neuron. In another aspect, these population of cells can further comprise, or alternatively consist essentially of, or yet further consist of, an isolated spiral ganglia-like neuron (SGN). In one aspect, this cell is an isolated SGN or isolated SGN. The amount of proportion of each cell type will vary with the use of the composition.

The cells or populations of cells can be combined with agents that promote differentiation or promote the functional switch of ependymal cells, that include but are not limited to Brn3c, prestin, otoferlin, and CtBP2. Thus, this invention also provides a method to promote differentiation or the functional switch of ependymal cells by contacing a cell or population of cells as described herein with an effective amount of one or more of Brn 3c, prestin, otoferlin, or CtBP2. The contacting can be accomplished in vitro or in vivo by administration locally or systemically an effective amount of the one or more of Brn 3c, prestin, otoferlin, or CtBP2. These agents are commercially available or can be prepared using publicly available sequence information and conventional techniques such as PCR. The method can further comprise, or alternatively consist essentially of, or yet further consist of, isolating or separating the differentiated cells from the undifferentiated cells using immunohistochemical techniques such as a cell sorter.

Also provided by this invention is a population of differentiated cells produced by propagating the above-noted isolated cell(s) or substantially homogeneous population of cells. In one aspect, the cells and/or populations are propagated by culturing in vitro or in vivo with HCs and/or SGNs.

Any one or more of the above isolated cell, modified cell or population of cells can be combined with a carrier, such as a pharmaceutically acceptable carrier. In one aspect, the amount of cells in the composition is an effective amount to obtain a determined diagnostic use or therapeutic benefit as described herein or known to those of skill in the art.

Also provided by this invention is an animal model comprising any one or more of the above isolated cell, modified cell or population of cells. Further provided is a method of producing an animal model by administering to the animal an effective amount of the above isolated cell, modified cell or population of cells. Methods of administering cells or cell compositions are known in the art and briefly described herein. This animal models can be used to screen for potential therapeutic or diagnostic agents.

Methods to Produce Modified Cells and Populations of Cells

Also provided by this invention are methods to isolated and produce the cells, modified cells and population of cells as described herein. A population or isolate from the LV and/or CP of a subject is contacted with an antibody or other marker-specific composition under conditions that favor the formation of a marker-antibody (or other specific composition) complex, and then isolating the complex from the composition having non-complexed cells and antibody. Confirmation of cell type can be accomplished as described herein.

This invention also provides methods for the insertion of polynucleotides and/or genetic modification of the source cell or population by modulation of the expression of one or more genes. In one aspect, such modification is achieved by inserting a polynucleotide encoding the gene into the cell or population by any suitable method. For example, the polynucleotide of interest is inserted into a vector such as a viral vector which is then contacted with the cell or population under conditions that facilitate transfer of the vector and polynucleotide into the cell. The recipient cell is grown or propagated under suitable conditions to express the inserted gene. In other aspects, the cell or population is modified to enhance expression of the endogenous gene of interest. In further aspects, the genes are overexpressed as compared to a wild-type counterpart cell by inserting numerous copies of the polynucleotide or alternatively, enhancing expression of the endogenous gene of interest. In the embodiment where the modification is reduced expression. In one aspect, the gene of interest encodes a detectable marker such as GFP.

Gene Expression and Nucleic Acids

In order to express exogenous proteins described herein, delivery of nucleic acid sequences encoding the gene on interest can be delivered by several techniques. Examples of which include viral technologies (e.g. retroviral vectors, adenovirus vectors, adeno-associated virus vectors, alphavirus vectors and the like) and non-viral technologies (e.g. DNA/liposome complexes, and targeted viral protein-DNA complexes). Once inside the cell of interest, expression of the transgene can be under the control of ubiquitous promoters (e.g. EF-1α) or tissue specific promoters. Alternatively expression levels can be controlled by use of an inducible promoter system (e.g. Tet on/off promoter).

This invention also provides genetically modified cells that produce enhanced expression of the genes of described herein or their equivalents. The genetically modified cells can be produced by insertion of upstream regulatory sequences such as promoters or gene activators (see, U.S. Pat. No. 5,733,761).

Non-limiting examples of promoters include, but are not limited to, the cytomegalovirus (CMV) promoter (Kaplitt et al. (1994) Nat. Genet. 8:148-154), CMV/human β3-globin promoter (Mandel et al. (1998) J. Neurosci. 18:4271-4284), GFAP promoter (Xu et al. (2001) Gene Ther., 8:1323-1332), the 1.8-kb neuron-specific enolase (NSE) promoter (Klein et al. (1998) Exp. Neurol. 150:183-194), chicken beta actin (CBA) promoter (Miyazaki (1989) Gene 79:269-277) and the β-glucuronidase (GUSB) promoter (Shipley et al. (1991) Genetics 10:1009-1018), the human serum albumin promoter, the alpha-1-antitrypsin promoter. To improve expression, other regulatory elements may additionally be operably linked to the transgene, such as, e.g., the Woodchuck Hepatitis Virus Post-Regulatory Element (WPRE) (Donello et al. (1998) J. Virol. 72: 5085-5092) or the bovine growth hormone (BGH) polyadenylation site.

Additional promoters which are suitable for the present invention may be any strong constitutive or tissue (neural)-specific promoter which is capable of promoting expression of an associated coding DNA sequence in neuronal tissue.

In addition to the expression of genes described herein, the down regulation of presently existing genes within the cell can be utilized. "Reducing expression" or "down regulating expression" is a process resulting in the decreased gene and corresponding protein expression. For example, when a cell is overly stimulated by a neurotransmitter, hormone or drug for a prolonged period of time and the expression of the receptor protein is decreased in order to protect the cell. Reducing expression of a gene described herein can be done by a variety of method known in the art. Examples of which include the use of oligonucleotide-based strategies including interfering RNA technology, micro-RNA, siRNA, and vector based technologies including insertional mutagenesis, Cre-Lox deletion technology, double-stranded nucleic acid RNA/RNA, DNA/DNA, RNA/DNA and the like.

Polynucleotides useful for the methods of this invention can be replicated using PCR. PCR technology is the subject matter of U.S. Pat. Nos. 4,683,195; 4,800,159; 4,754,065; and 4,683,202 and described in PCR: The Polymerase Chain Reaction (Mullis et al. eds, Birkhauser Press, Boston (1994)) and references cited therein.

Detection

One can determine if the required expression, overexpression or underexpression of the polynucleotide of interest has been achieved by using methods known in the art, e.g., by traditional hydridization techniques, immunohistochemistry using a cell sorter (FACs) or PCR. Specific examples include hybridization to DNA microarrays, in situ hybridization, PCR, RNase protection assays and Northern blot analysis. Alternatively expression of the encoded polypeptide can be detected using antibodies that specifically recognize and bind the polypeptide or protein. Such antibodies are useful for visualizing cells that express the polypeptide using techniques such as immunohistology, ELISA, and Western blotting.

As used herein, an "antibody" includes whole antibodies and any antigen binding fragment or a single chain thereof. Thus the term "antibody" includes any protein or peptide containing molecule that comprises at least a portion of an immunoglobulin molecule. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein, any of which can be incorporated into an antibody of the present invention. The term "antibody" is further intended to encompass digestion fragments, specified portions, derivatives and variants thereof, including antibody mimetics or comprising portions of antibodies that mimic the structure and/or function of an antibody or specified fragment or portion thereof, including single chain antibodies and fragments thereof. Examples of binding fragments encompassed within the term "antigen binding portion" of an antibody include a Fab fragment, a monovalent fragment consisting of the $V_L$, $V_H$, $C_L$ and CH, domains; a F(ab')2 fragment, a bivalent fragment comprising two Fab fragments linked by a disulfide bridge at the hinge region; a Fd fragment consisting of the $V_H$ and $C_H$, domains; a Fv fragment consisting of the $V_L$ and $V_H$ domains of a single arm of an antibody, a dAb fragment (Ward et al. (1989) Nature 341:544-546), which consists of a $V_H$ domain; and an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv)). Bird et al. (1988) Science 242:423-426 and Huston et al. (1988) Proc. Natl. Acad Sci. USA 85:5879-5883. Single chain antibodies are also intended to be encompassed within the term "fragment of an antibody." Any of the above-noted antibody fragments are obtained using conventional techniques known to those of skill in the art, and the fragments are screened for binding specificity and neutralization activity in the same manner as are intact antibodies.

Various antibody preparations can also be used in analytical methods such as ELISA assays or Western blots to demonstrate the expression of proteins encoded by the identified genes by test cells in vitro or in vivo. Fragments of such proteins generated by protease degradation during metabolism can also be identified by using appropriate polyclonal antisera with samples derived from experimental samples.

Use of the Cells and Cell Populations

The cells, populations or compositions are useful for reconstituting cochlear sensory epithelia or alternatively, hair cells or SGNs in a subject in need thereof, by administering an effective amount of the isolated cells or populations as described herein to a subject at the anatomical site in the subject in need thereof. The cells can be autologous or allogeneic to the subject.

In another aspect, the cells, populations or compositions are useful to treat a neural degenerative disease or alleviate the symptoms of the disease by administering an effective amount of the isolated cells, populations or compositions to a subject at the anatomical site with a degenerated neuron, thereby treating the disease or alleviate the symptom of the disease. The cells can be autologous or allogeneic to the subject. Examples of neural degenerative diseases include, but are not limited to sensorineural hearing loss, occupational-induced hearing loss, neonatal and progressive hearing loss, age-induced hearing loss, drug-induced hearing loss, noise-induced hearing loss, traumatic inner ear diseases and vestibular disorder related to inner ear disorders. Drugs and therapies that may cause hearing loss include, but are not limited to the antibiotics aminoglycosides (streptomycin or neomycin), vancomycin, the platinum-containing drugs used to treat cancer such as oxaliplatin, cisplatin or carboplatin, diuretics such as ethacrynic acid (Edecrin™) or furosemide (Lasix™), Quinine (Qualaquin™) or salicylates. Traumatic inner ear diseases that may be treated or the symptoms of which may be alleviated include, without limitation acoustic neurinoma, decompression of trigeminal neuralgia, and fracture of the auditory ossicles.

In addition, the cells, populations or compositions can be administered to a subject in need thereof to provide renewable cells derived from the same germ layer to fill the vacancy of nonrenewable-highly differentiated sensorineural cells by reprogramming their functions to adapt the new environment. They also can be used to provide stable secretion of neuroprotective cocktail, escaping immune rejection by autologous transplantation, thereby making the isolated choroid plexus cells the appealing choice for spiral ganglion neurons. The cells can be autologous or allogeneic to the subject. The neuroprotective capability of choroid plexus cells can extend to design novel therapeutic strategies targeting neurodegenerative diseases.

Administration of the cells or compositions can be effected in one dose, continuously or intermittently throughout the course of treatment. Methods of determining the most effective means and dosage of administration are known to those of skill in the art and will vary with the composition used for therapy, the purpose of the therapy and the subject being treated. Single or multiple administrations can be carried out with the dose level and pattern being selected by the treating physician. Suitable dosage formulations and methods of administering the cells, populations or compositions are known in the art.

The cells and populations of cell are administered to the host using methods known in the art and briefly described herein.

Screening Assays

The present invention provides methods for screening various agents that modulate cell function of a cell or population of cells of this invention. For the purposes of this invention, an "agent" is intended to include, but not be limited to a biological or chemical compound such as a simple or complex organic or inorganic molecule, a peptide, a protein (e.g. antibody), a polynucleotide (e.g. anti-sense) or a ribozyme. A vast array of compounds can be synthesized, for example polymers, such as polypeptides and polynucleotides, and synthetic organic compounds based on various core structures, and these are also included in the term "agent." In addition, various natural sources can provide compounds for screening, such as plant or animal extracts, and the like. It should be understood, although not always explicitly stated that the agent is used alone or in combination with another agent, having the same or different biological activity as the agents identified by the inventive screen.

One aspect of the invention is a method for screening small molecules capable of modifying the cell or population of this invention. For the purpose of this invention, "small molecules" are molecules having low molecular weights (MW) that are, in one embodiment, capable of binding to a protein of interest thereby altering the function of the protein. Preferably, the MW of a small molecule is no more than 1,000. Methods for screening small molecules capable of altering protein and/or polynucleotide function are known in the art. For example, a miniaturized arrayed assay for detecting small molecule-protein interactions in cells is discussed by You et al. (1997) Chem. Biol. 4:961-968.

To practice the screening method in vitro, suitable cell cultures or tissue cultures containing the cell or population is first provided. When the agent is a composition other than a DNA or RNA, such as a small molecule as described above, the agent can be directly added to the cell culture or added to culture medium for addition. As is apparent to those skilled in the art, an "effective" amount must be added which can be empirically determined. When agent is a polynucleotide, it can be directly added by use of a gene gun or electroporation. Alternatively, it can be inserted into the cell using a gene delivery vehicle or other method as described above. Positive and negative controls can be assayed to confirm the purported activity of the drug or other agent.

The agents can be assayed in vitro by administering to an appropriate animal model the cell or population of cells under conditions that favor differentiation (as described herein) and then administering to the animal, systemically or locally, the agent to be tested. Positive or negative control animal models can be provided as known in the art, having an agent with the desired effect (positive control) and an animal that does not receive any agent (negative control).

The following examples are intended to illustrate and not limit the inventions as provided herein.

EXPERIMENTAL EXAMPLES

Example 1

Cells of Adult Brain Germinal Zone have Properties Akin to Hair Cells and can be Used to Replace Inner Ear Sensory Cells after Damage Methods The care and use of animals in this study was approved by the Ethical Committees at the University of California, Davis. C57BL/6j mice were purchased from Charles River Laboratories.

Generation of transgenic mouse line: Myosin VIIA-GFP was generated as previous reported (21).

Culture of adult neural stem cells: Neurospheres were generated as previously described and as known in the art (42). Neuronal differentiation was enhanced with 2 µM retinoic acid.

Co-culture of SGNs with ependymal cells: Target deprived adult SGNs (from C57BL/6j mice) were isolated as described (5) and co-cultured with ependymal cells prepared from myosin VIIAGFP mice.

Co-culture of NSC derived neurons and hair cells: NSC-derived neurons were obtained as described above. The organ of Corti was isolated from p3-5 mice, and residual SGNs were eliminated by treatment with β-Bungarotoxin (Sigma, 0.5 µM) for 48 hours.

Scanning Electron Microscopy (SEM) and Transmission Electron Microscopy (TEM). The lateral wall of the LV was dissected then fixed with 2.5% glutaraldehyde and 2% paraformaldehyde. For SEM, samples were dehydrated, critical point dried and infiltrated with gradient hexamethyldisilazane, then mounted on stubs and sputter coated with gold-palladium. Images were collected on a Philips FEI XL30 SEM. For TEM, samples were postfixed in 1% osmium tetroxide, dehydrated, infiltrated, and polymerized. Ultrathin sections were post-stained. Images were taken on a Philips EM400 TEM with a MegaView digital camera (Soft Imaging Systems, Inc.).

Immunohistochemistry. Cultures were fixed with 4% paraformaldehyde in PBS (PBS) for 20 min, then rinsed and immunostained with antibodies directed against mouse and rabbit anti tubulin III (Tuj1) (BAbco), mouse anti-neurofilament 200 (Sigma), mouse anti-NeuN (Chemicon), mouse anti-synapsin 1 (SY), rabbit anti-glial fibrillary acidic protein (GFAP) (DAKO), mouse anti-glial fibrillary acidic protein (Chemicon), rabbit anti-myosin VIIA and myosin VI (Proteus Biosciences), mouse anti-CtBP2 (BD), chicken anti-GFP (Chemicon) and rat anti-BrdU (Accurate Chemical & Scientific Corporation), following standard protocols. Immunostaining was visualized with secondary antibodies conjugated to Cy3, Cy5, or Alexa Fluor 488, 548, or 647 fluorophores. Regular immunohistochemistry staining followed biotin-streptavidin-diaminobenzidine protocols. Omission of the primary antibodies eliminated staining in all preparations examined. The nucleus was counterstained with DAPI. A Zeiss LSM 510 Meta confocal microscope or an Olympus fluorescent microscope equipped with a digital camera was used to collect images. Imaris Bitplane software was used to generate 3D reconstructions of confocal Z-stack images.

BrdU Administration and Immunofluorescence. To demonstrate the in vivo proliferation of ependymal cells, BrdU (100 mg/kg in 0.9% NaCl) was injected i.p. into C57BL/6j mice (8-10 weeks old, Charles River) once a day for 30 days before sacrifice. Animals were then anesthetized and killed by cervical dislocation, whereafter their brains were flash-frozen with dry ice and then cryosectioned. For the in vitro proliferation test of ependymal cells, BrdU was added to the culture medium 48 h after initial culture (5 mM) and was maintained for 72 h. BrdU and myosin VIIA double staining followed the protocol as described (5). Omission of the primary antibodies eliminated staining Double-labeled ependymal cells were confirmed by serial confocal sectioning.

Assay for Mechanosensory Transduction in Ependymal Cells. Animals were killed by cervical dislocation then the lateral wall of LV was exposed to 5 mM FM1-43FX (Molecular Probes) for 60 s and fixed with 4% formaldehyde. A thin layer of the lateral wall was dissected and mounted to examine the fluorescent intensity to determine dye uptake. To block the entry of FM1-43, the lateral ventricle was preincubated and repeatedly flushed with DHS for 4 min.

Electrophysiology. Hair cells were identified by the presence of green fluorescence under UV light. NSC-derived neurons were identified by their distinct neuronal morphology of a small, round and phase bright cell body with long uneven processes. Spiral ganglion neurons were identified by their much larger round and phase bright cell bodies and unipolar and/or bipolar neurites. The criteria were confirmed by immunostaining in parallel cultures. Currents were amplified with an Axopatch 200B amplifier (Axon Instruments) and filtered at a frequency of 2-5 kHz through a low-pass Bessel filter. The data were digitized at 5-500 kHz using an analog-to-digital converter (Digidata 1200; Axon Instruments). The sampling frequency was determined by the protocols used. Action potentials were amplified (100×), filtered (bandpass 2-10 KHz), and digitized at 5-500 kHz using the Digidata 1200 as described earlier. The extracellular solution for most experiments contained (in mM) NaCl 145, KCl 6, $MgCl_2$ 1, $CaCl_2$ 0-2, D-glucose 10, and Hepes 10, at pH 7.3. For perforated patch experiments, the tips of the pipettes were filled with an internal solution containing (in mM): KCl 150, Hepes 10, and D-glucose 10, at pH 7.3. The pipettes were front-filled with the internal solution and back-filled with the same solution containing 250 mg/ml amphotericin. Stock solutions were reconstituted and perfused in the recording chamber. CNQX (5 mM) was used to block AMPA receptors.

Results

The embryonic germinal zone in the adult forebrain lateral ventricle (LV) region contains two morphologically distinct cell layers: the ependymal layer contains ciliated epithelial cells and the subventricular zone (SVZ), beneath the ependymal layer, hosts multipotential neural stem cells of active neurogenesis (9). A subpopulation of cells with astrocytic characteristics within the SVZ (10-13) has become the source of adult neural stem cells (NSCs) lining the LV, to produce both neurons and glia. Most intriguingly, there are phylogenetic lineage relationships between the adult forebrain germinal zone cells and the sensory and non-sensory epithelia of the inner ear. Both are derived from the neural ectodermal layer and share certain protein markers that are expressed within the organ of Corti and SGNs (14, 15). In addition, the cilia of forebrain ependymal cells are microtubular structure and actin-filled process as in the HCs.

Ependymal cells adjacent to the spinal canal proliferate extensively upon spinal cord injury (16, 17). Proliferation of adult brain LV ependymal cells (18) can also be detected following a stroke. Although previous studies fail to detect cell proliferation in these ependymal cells under physiological conditions (19), active proliferation of LV ependymal cells has been confirmed in several experiments, in vitro (11, 20). In the present study, it is shown that LV ependymal cells demonstrate proliferative capacity both in vitro and in vivo; and most importantly, they have the potential to give rise to inner ear hair cell-like phenotypes. These cells share many morphological and functional characteristics with inner ear HCs, including, stereociliary and kinociliary bundles, expression of hair cell markers, selective uptake of FM1-43 dye, and they are also able to establish functional synapses with primary SGNs. Moreover, the SGN-like neuronal progenies could be derived from SVZ neural stem cells residing underneath the ependymal layer. These neuronal progenies establish functional synapses with HCs and deafferentated SGNs. Thus, within the adult forebrain germinal zone, ependymal and subependymal cells can undergo an epigenetic functional switch that could potentially enable them to replace damaged HCs and SGNs in the auditory setting.

Figure 2:
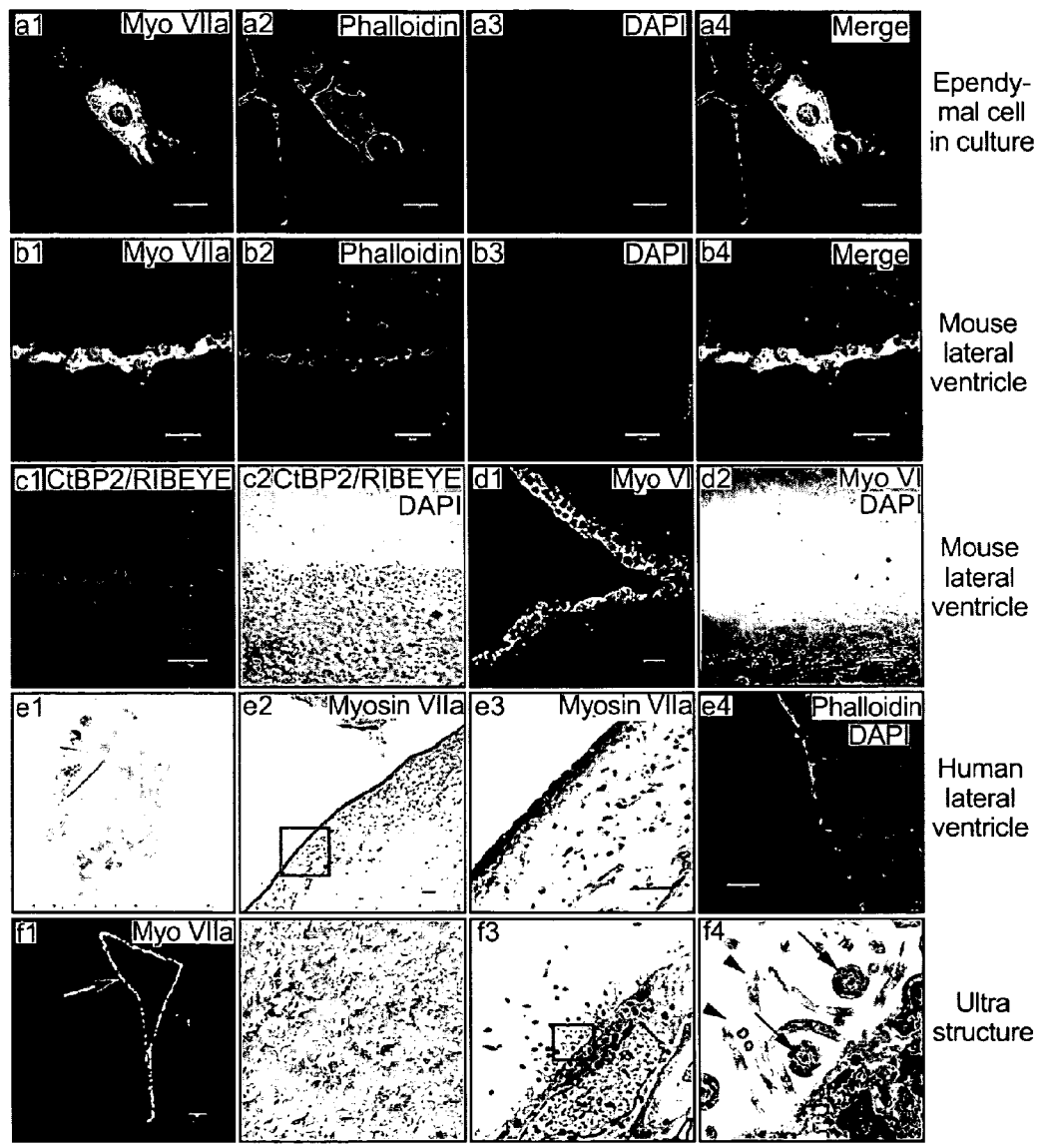
FIG. 2 shows in vitro and in vivo structural profile of adult ependymal cells. (a1-a4) Cultured adult ependymal cells remain myosin VIIA-positive (a1). Phalloidin-labeled actin-rich sterocilialike appendages were found on the apical surface of the cells (a2). (b1-d2) Cryosection of the lateral wall of the LV of adult mice. Ependymal cells were clearly and specifically labeled with myosin VIIA (b1) and phalloidin (b2-b4). Hair cell synaptic protein CtBP2/RIBEYE was observed in ependymal cells of the LV (c1, c2). The ependymal cell layer of the LV also expressed myosin VI, an early HC marker (d1-d2). Myosin VI-positive cells are shown in white (d1), whereas the nuclei stain is in gray. The light microscope and merged image are represented in (d2). (e1-e4) Myosin VIIA was expressed in adult human ependymal cells. Panel (e1) is a photomicrograph of a normal adult human brain sliced and frozen within 18 hours of death. Postmortem, a wedge around the LV region was taken from the brain then fixed, sectioned and stained to provide panels (e2-e4). The dashed lines indicate the LV region (e1). Adult human ependymal cells also expressed myosin VIIA (e2). The boxed area of panel (e2) is enlarged in panel (e3) to demonstrate myosin VIIA expression. Phalloidin-labeled actin stereocilia-like appendages were found on the apical aspects of human ependymal cells (e4). Scanning (f2) and transmission electron microscopy (f3) of the lateral ventricle region (arrow in f1) demonstrated that ependymal cells are also equipped with structural profiles of stereocilia and kinocilia, similar to HCs. The boxed area of panel (f3) was enlarged in panel (f4), showing stereociliary appendages (arrow heads) and the characteristic 9+2 microtuble structure of kinocilia (arrows). The nuclei were labeled with DAPI. (a3, a4, b3, b4, c2, d2, e4). Scale bars: a1-d2, e4, f2=20 μm, f1, e2-e3=100 μm.

The Ependymal Layer of the LV Contains Cells that Display HC Characteristics and Proliferative Potential Myosin VIIA has been previously identified as a hair-cell marker (21, 22) and is widely used in hair cell differentiation and regeneration studies (23). Unexpectedly, in in vitro cell culture characterization and expansion studies, neurospheres obtained from the LV of transgenic mice expressing the green fluorescent protein (GFP) under the control of MyoVIIA promoter (21), contained small GFP positive colonies (FIG. 1a1). Expression of myosin VIIA in these colonies was confirmed with immunofluorescent staining (FIG. 1a2-a4). To provide evidence that the ependymal cells may proliferate, BrdU immunocytochemistry was performed with these cultures. As shown in FIG. 1 (b1-b4), some of the myosin VIIA-positive cells were also BrdU positive, indicating their in vitro proliferative capacity. However, they were distinct from the newly differentiated neurons derived from the same neurosphere, as those neurons expressed the neuronal marker, TuJ1. Next, to identify the cell type that expresses myosin VIIA and to determine whether they have proliferative potential in situ, the lateral ventricular cells were examined in BrdU-treated adult mice. Robust and specific staining of myosin VIIA was only observed in the polarized ependymal cells (supplementary (s) FIG. 6), some of which were also BrdU positive, demonstrating that the cells proliferate in vivo (FIG. 1c1-c4).

To test whether ependymal cells can assume the HC-structural phenotype, immunostaining for myosin VIIA and phalloidin staining for F-actin were performed. In culture, ependymal cells are columnar shape, remain myosin VIIA-positive and extend appendages that are labeled with phalloidin, partially resembling HCs (FIG. 2a1-a4). However, since the in vitro culture environment may be slightly different from in vivo conditions (24), the expression of myosin VIIA and actin-based appendages in the ependymal cell layer of brain slices was then examined.

Figure 3:
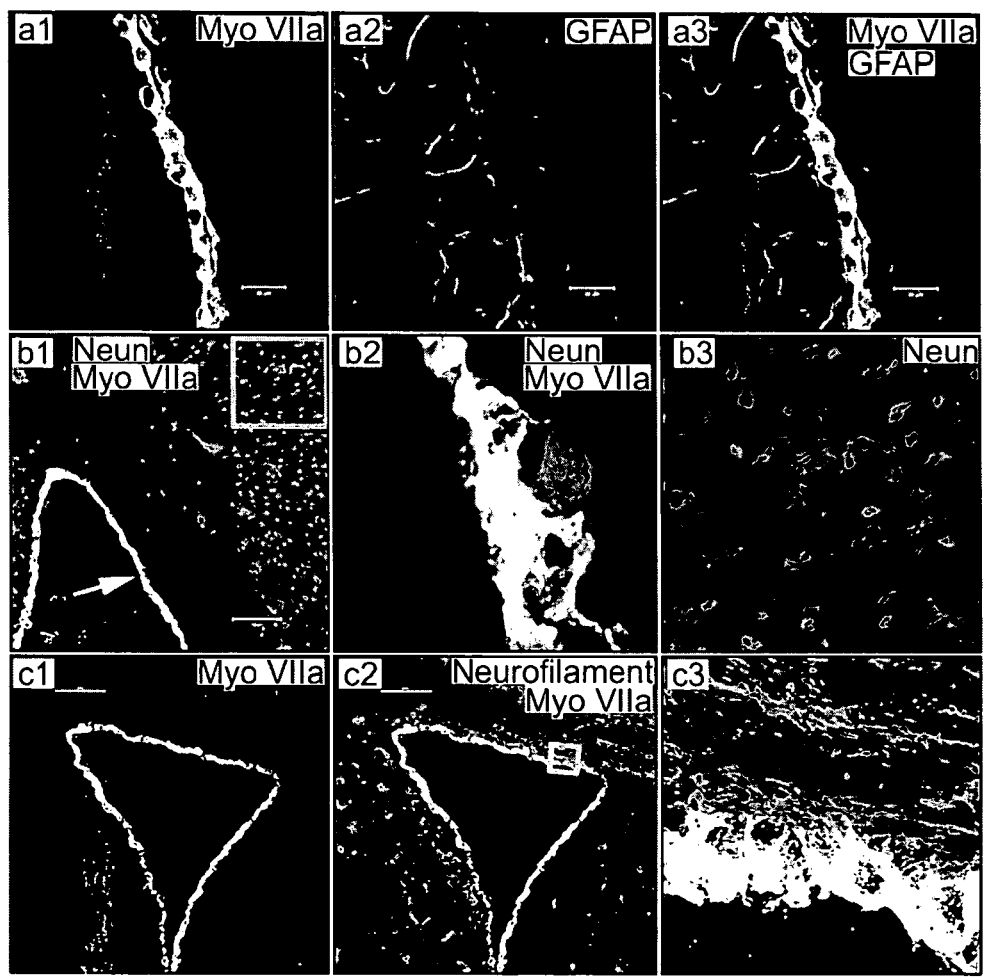
FIG. 3 shows that ependymal cells that were HC-marker positive, did not, in general, express glial cell and neuronal markers. Ependymal cells were labeled only with myosin VIIA (a1). GFAP demonstrated a distinct staining pattern in cells around ependymal cells (a2). Some GFAP positive cells extended to myosin VIIA positive ependymal cells (a3). Panel (b1) demonstrates that ependymal cells are not labeled with the mature neuronal marker, NeuN. Arrow indicates the nucleus of NeuN staining near an ependymal cell. The indicated area was enlarged in panel (b2), which shows that the NeuN labeling did not co-localize with ependymal cells. The rectangular area in panel (b1) was enlarged in panel (b3) to display the NeuN labeled neuronal cells. (c1-c3) To verify that ependymal cells display the HC-phenotype and not the neuronal phenotype, an adult mouse brain section was double stained with myosin VIIA and another mature neuronal marker, neurofilament. Ependymal cells were specifically labeled with myosin VIIA (c1), but not neurofilament (c2). The panel shows neurofilament-positive nerve fibers in the LV. The rectangle area in panel (c2) was re-scanned and enlarged in panel (c3), showing a projected image of serial scanned image frames. Panel (c3) not only demonstrates that ependymal cells do not express neuronal markers, it shows that nerve fibers make contacts with ependymal cells, in vivo. Scale bars: a1-a3=20 μm, b1, c1, c2=100 μm.
Figure 6:
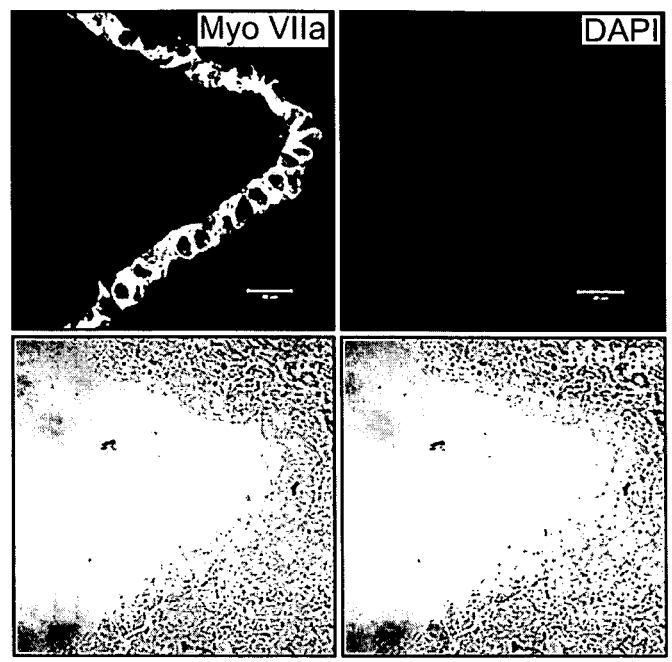
FIG. 6 shows adult brain ependymal cells take the shape of polarized columnar epithelial cells and express myosin VIIA. (Scale bar, 20 µm.)

Consistent with the in vitro scenario, the apical cellular layer of the LV was positively labeled with myosin VIIA and phalloidin (FIG. 2b1-b4). To provide further evidence that these ependymal cells resemble inner ear hair cells, immunostaining was performed with additional hair cell markers including ribeye, a hair cell synaptic protein (25), and myosin VI (22). As shown in FIG. 2c1-d2, ribeye and myosin VI were also expressed by cells of ependymal layer (FIG. c1-d2). Furthermore, the expression of myosin VIIA and clusters of actin based appendages in the ependymal layer cell were not restricted to the nervous system of mice alone, but was found in humans as well, providing assurance that these findings transcend species-specific phenomena (FIG. 2e1-e4). Moreover, scanning and transmission electron microscopy was used to examine the ultra structures at the apical aspects of ependymal cells. This analysis confirmed that the ependymal cell is lined with cillary appendages made of stereocilia and kinocilia, reminiscent of vestibular HCs in the inner ear (FIG. 2f1-f4). It is important to emphasize that the myosin VIIA-positive cells were only found in the ependymal layer of the LV, they are neither like glial cells nor neurons. Instead, they are columnar; take the shape of polarized epithelial cells (FIG. 6). These myosin VIIA-positive cells are distinct from glial cells and neurons, since they did not stain positively for the glial cell marker, glial fibrillary acidic protein (GFAP) (FIG. 3a1-a3), and neuronal markers, such as NeuN (FIG. 3b1-b3) or Neurofilament (FIG. 3c1-c3). Only a few end feet of glial cells could be seen extending to the ependymal cell layer, which surrounded the myosin VIIA labeled cell bodies, but did not penetrate into the cell's cytoplasmic region. These results clearly indicate that these myosin VIIA-positive ependymal cells are neither neurons nor glial cells, but rather distinct epithelial cell-types.

Figure 4:
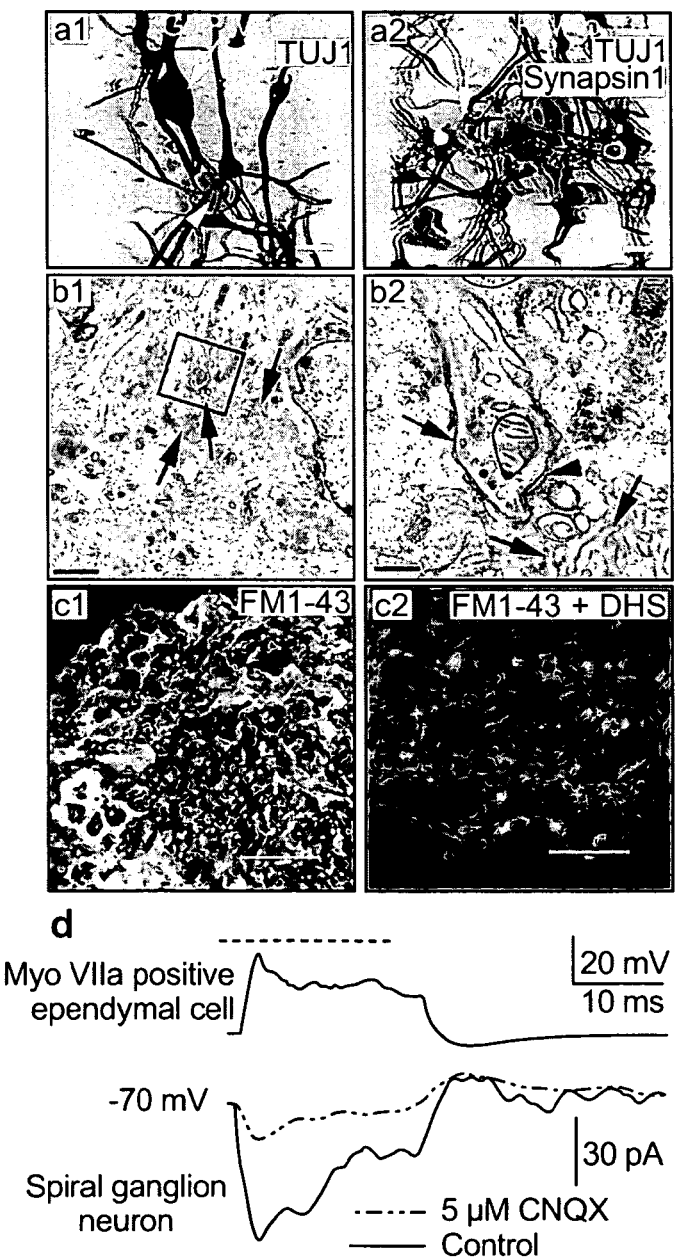
FIG. 4 shows that spiral ganglion neurons targeted myosin VIIA-positive ependymal cells to establish functional synaptic contacts. Adult SGNs and ependymal cells were co-cultured to test whether they could recognize each other as the targets. To eliminate the possibility that the co-cultured myosin VIIA positive cells may originate from inner ear HCs, ependymal cells were collected from myosin VIIA-GFP transgenic mice and SGNs were collected from wild type mice (C57BL/6j), therefore, GFP staining in this figure indicates myosin VIIA positive ependymal cells. (a1) Shown is a 3-D reconstruction image of an adult SGN (arrow) projecting neurites to an ependymal cell (arrowhead). (a2) This panel demonstrates an enlarged nerve ending of an adult SGN connected to a cluster of ependymal cells. The accumulation of synapsin 1 at the enlarged nerve endings (arrow) of the adult SGN suggests that connections between SGNs and ependymal cells may form synapses. (b1-b2) Ultra structure of synapses was found between cocultured SGNs and ependymal cells. The boxed area in panel (b1) demonstrates the synaptic ultra structure between a SGN and an ependymal cell, which is enlarged in panel (b2) to show detail. The black arrowhead indicates the post-synaptic thickenings. The ependymal cell can be identified by its signature structure; the clustered cilia (black arrows). The gray arrow on the upper left indicates a nerve ending of the SGN. (c1) Merged transparent and fluorescence images of ependymal cells obtained after 60-sec exposure to FM1-43. Similar results were obtained using shorter exposure time (<30 s; data not shown). (c2) FM1-43 loading of ependymal cells was inhibited following pre-exposure of the transduction channel blocker, dihydrostreptomycin (DHS) (240 sec; n=6). (d) Dual recording from the connected myosin VIIA-positive ependymal cell (in current-clamp mode; 0.4 nA current injection) and SGN (in voltage-clamp at −70 mV holding potential). The synaptic current recorded in the SGN was sensitive to CNQX (dashed line), an AMPA receptor blocker. Scale bar a1-a2, c1-c2=20 μm; b1=2 μm, b2=7 μm.
Figure 7:
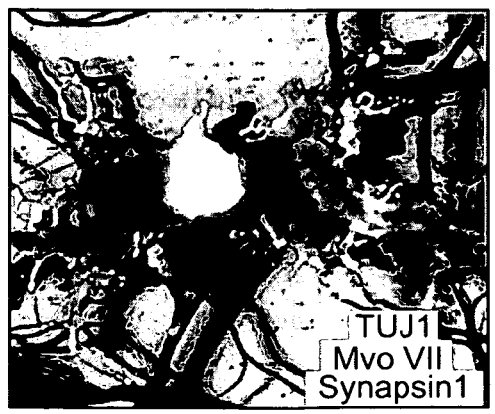
FIG. 7 shows accumulation of synapsin 1 at the nerve fibers focused around the ependymal cells revealed that contacts among NSC-derived neurons and ependymal cells have the potential to develop into synapses. Shown is an enlarged region of FIG. 4A2, depicting the accumulation of synapsin 1 at the adult SGN nerve endings. (Scale bar, µ20 m.)

Myosin YHA-positive ependymal cells show functional characteristics of HCs and can incorporate into cochlear sensory epithelia. To further identify functional similarities between myosin VIIA-positive ependymal cells and inner ear HCs, were co-cultured the ependymal cells from myosin VIIA-GFP transgenic mice with SGNs prepared from wild type mice. Ependymal cells established synapse-like contacts with SGNs (FIG. 4a1). Robust staining of synapsin 1 was observed at the sites of contact (FIG. 4a2; see enlarged image in FIG. 7). Transmission electron micrographs of serially sectioned cells illustrated characteristic synaptic structures such as presynaptic vesicles, pre/post-synaptic membrane-associated density and synaptic thickening, and a specialized synaptic cleft (FIG. 4b1-b2). Another similarity between ependymal cells and HCs is that ependymal cells express partially open large-conductance cation channels that are permeable to FM1-43 akin to mechanosensitive channels in hair cells. Ependymal cells show rapid (<60 s) FM1-43 uptake, which was inhibited by dihydrostreptomycin(26,27) (FIG. 4c1-c2). Finally, exemplary responses between myosin VIIA-positive ependymal cells (in 3 out of 7 synapses) and SGNs (FIG. 4d) were recorded. The fact that these synaptic responses were sensitive to a glutamate receptor blocker, CNQX (FIG. 4d), gives further credence to the tantalizing possibility that these in vitro results may mimic in vivo conditions (28).

Figure 8:
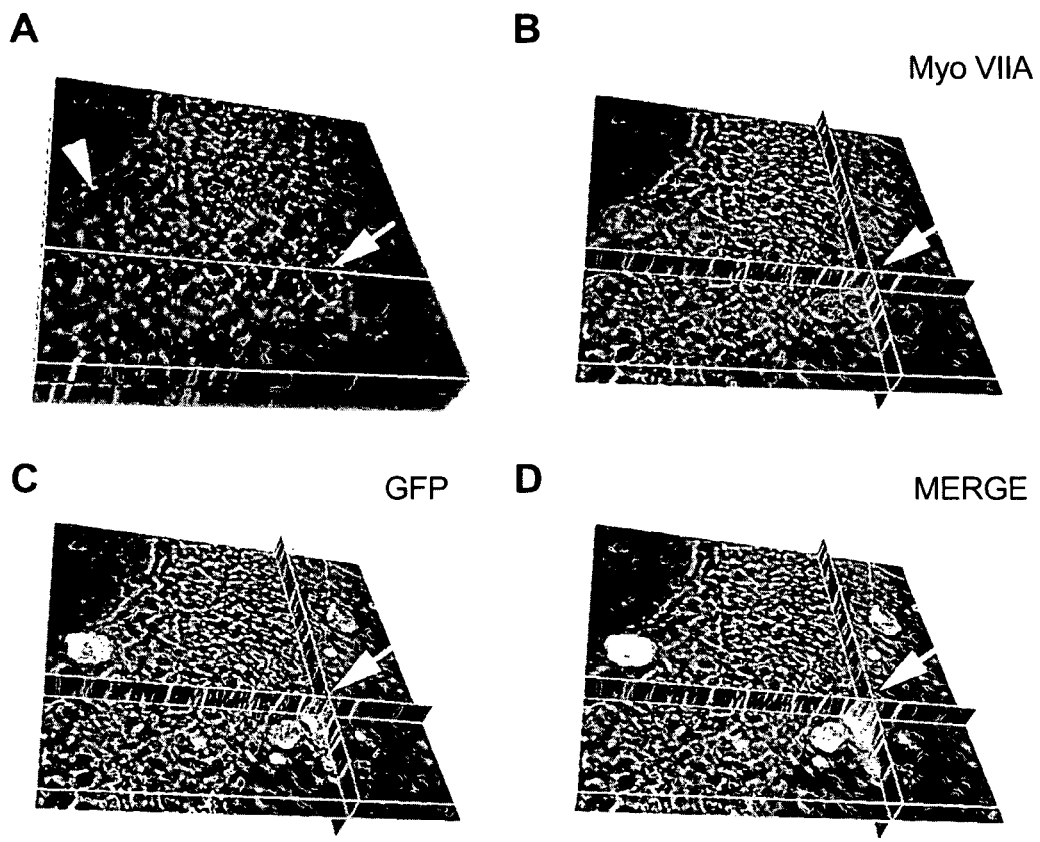
FIG. 8 shows incorporation of ependymal cells into cochlear sensory epithelia. Cochlear sensory epithelia were dissected from wild type mouse (C57 BL/6), and residual HCs were eliminated using streptomycin treatment. Ependymal cells were isolated from myosin VIIA-GFP transgenic mouse line. Cochlear sensory epithelia and ependymal cells were co-cultured for 5 days. (A) 3D reconstruction of co-cultured inner ear sensory epithelia and ependymal cells. Small patch of ependymal cells incorporated into the inner (arrowhead) and outer (arrow) marginal portion of the sensory epithelia. To demonstrate this incorporation clearly, an x axis (indicated by vertical lines) and a y axis (indicated by horizontal lines) section were made across the incorporated ependymal cells. A section also was made along the mid point of the z axis (indicated by short lines perpendicular to the x-y plane). The detailed demonstration was illustrated in (B-D). (B) incorporated ependymal cells were stained with hair cell marker myosin VIIA, to show that the myosin VIIA-positive cells were incorporated ependymal cells, not the remaining cochlear hair cells which are also myosin 7a positive. The co-cultures also were stained with GFP, as shown in (C and D), the myosin VIIA-positive cells were also labeled with GFP, demonstrating that they are ependymal cells derived from myosin VIIA-GFP transgenic mouse.

Finally, to test whether ependymal cells can incorporate into cochlear sensory epithelia, these cells were dissected from wild type mouse (C57 BL/6) and the residual HCs were eliminated using streptomycin treatment. As shown in FIG. 8, ependymal cells incorporated well into the sensory epithelia, demonstrating their therapeutic potential.

Figure 5:
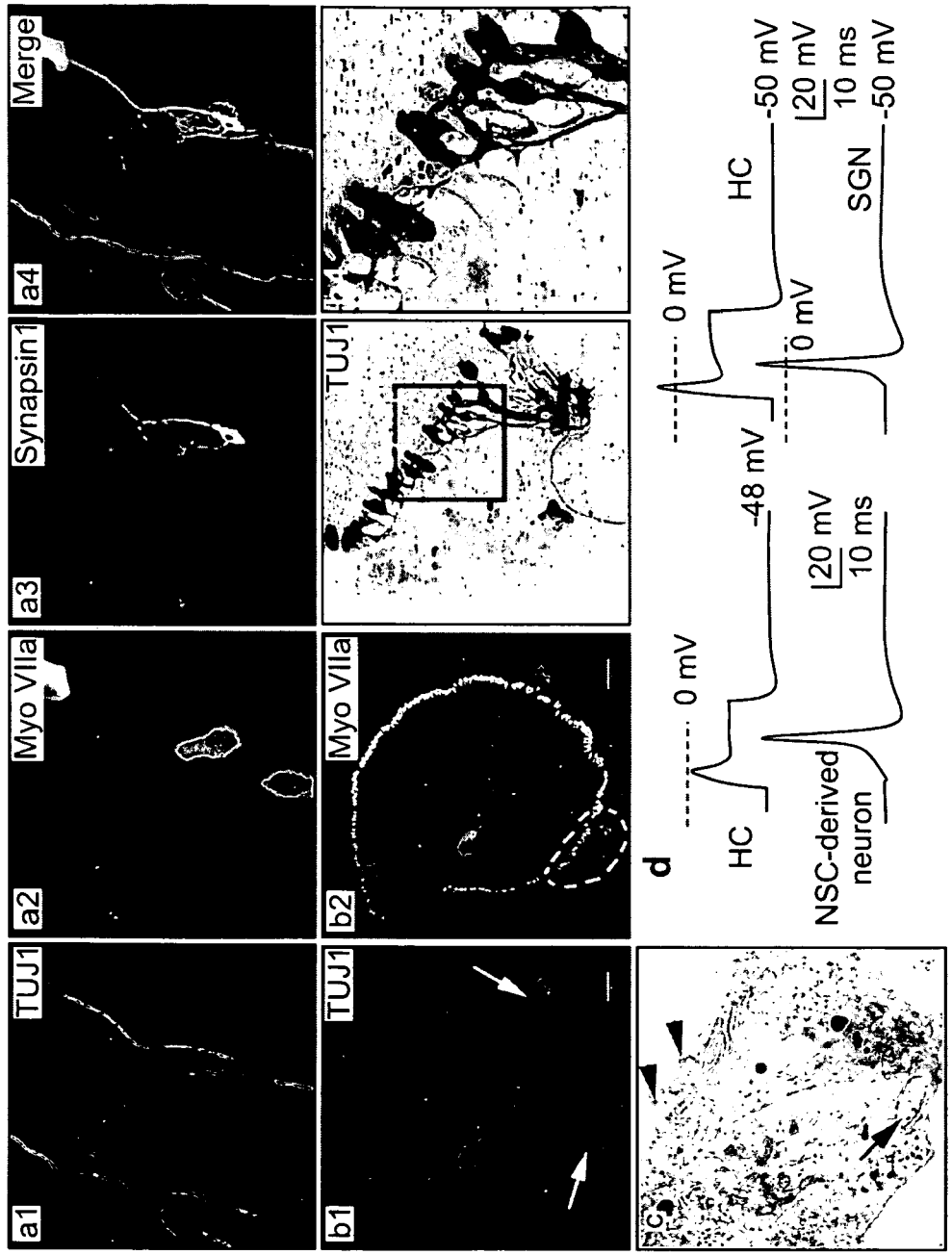
FIG. 5 shows that neural stem cell-derived neurons demonstrated defining characteristics of spiral ganglia neurons (SGNs). (a1-a4) Adult NSCs were co-cultured with hair cells (HCs). Nerve endings of a NSC-derived neuron in contact with a cocultured HC. The accumulation of synapsin 1 at the nerve ending suggests that the contact between NSC-derived neurons and HCs may develop into a real synapse. (b1-b4) NSC-derived neurons also established synapse-like contacts with HCs at the organ level. The organ of Corti was collected from P3 mice and SGNs were removed. To eliminate the residual SGNs, the dissected organ of Corti was treated with β-bungarotoxin (0.5 μM) for 48 hours then co-cultured with NSCs. Neuronal cells were labeled with TUJ1 and HCs were labeled with myosin VIIA. As panel (b1) demonstrates, residual SGNs were selectively removed from the organ of Corti following pre-treatment with β-bungarotoxin. Nerve fibers of NSC-derived neurons (arrows) penetrated the organ of Corti and established contacts with HCs (b2). The dashed line marks region in panel (b2) that was enlarged and reconstructed into a 3-D image in panel (b3); a cluster of NSC-derived neurons projected fibers into the organ of Corti and integrated with HCs. The accumulation of synapsin 1 indicates that the contacts between HCs and NSC-derived neurons may develop into synapses. The boxed area in panel (b3) was further enlarged in panel (b4) to show the synapse-like contacts. (c) Ultra structure of the nerve endings of a NSC derived-neuron that contacted co-cultured HCs (arrowheads indicate the stereocilia). Synaptic vesicles were found within the nerve ending (arrow). (d, left panel) Simultaneous current-clamp recordings from a HC and a NSC-derived neuron in close contact. The HC was injected with 0.7 nA positive current. The NSC-derived neuron was injected with a sustained negative current to establish a membrane potential of −83 mV. Under these conditions, sufficient depolarization of the HC elicited action potentials in the NSC-derived neuron.
Figure 9:
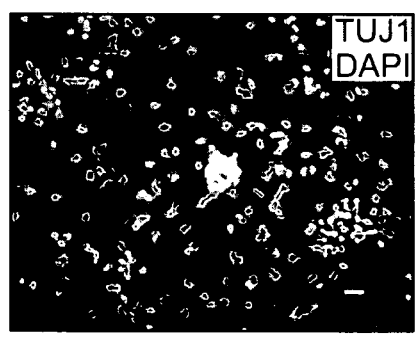
FIG. 9 shows neuronal differentiation of adult NSCs. (Scale bar, 20 µm.)

NSCs from LV differentiate into functional neurons with defining characteristics of SGNs. Here, whether NSCs from the SVZ, the very close neighbor of ependymal cell layer, were tested to determine if they can differentiate into neurons that share functional characteristics with SGNs. Following in vitro differentiation, 55+9% (mean+SD, n=9) of the NSCs isolated from the SVZ differentiated into neurons (FIG. 9). When co-cultured with inner ear HCs, these neurons projected neurites to HCs and synapsin 1 accumulated at the nerve ending, suggesting the development of real synapses (FIG. 5a1-a4). To further ascertain that NSC-derived neurons could establish synaptic contacts with HCs at the organ level, the organ of Corti was first dissected from the SGNs. The dissected organs of Corti were then incubated in β-bungarotoxin for 48 hours to eliminate a substantial portion of the residual SGNs (29). Next, seeds of predifferentiated NSCs were carefully placed at the abneural aspects of the organ culture (FIG. 5b1-b4). In accord with previous reports (29), β-bungarotoxin treatment eliminated most of the residual SGNs, as is reflected in minimal TUJ1 positive staining at the neural aspects of the organ of Corti (FIG. 5b1-b2). After seven days in vitro, NSC-derived neurons extended neurites to innervate HCs (FIG. 5b2-b4), fibers of NSC-derived neurons penetrated the organ of Corti making precise contact with HCs then stopping their growth and extension after reaching their targets. Also important, the branching pattern of neurites of NSC-derived neurons resembles a classic report by Retzius (30), whereby SGNs form multiple branches that undergo subsequent differential pruning. Hence, the in vitro innervation pattern of NSC-derived neurons on HCs resembles a microcosm of early development of cochlear ganglion neurons wherein neuronal fibers extend additional side branches, which are ultimately pruned in later neonatal stages (31). Synaptic connections between HCs and NSC-derived neurons were further verified by electron microscopic study. (FIG. 5c) Moreover, synaptic connections between HCs and NSC-derived neurons appeared functionally viable (FIG. 5d). Depolarization of HCs could elicit action potentials in neighboring NSC-derived neurons making synaptic contact. Similar responses were seen in adult SGNs (FIG. 5e), further establishing the authenticity and viability of these studies.

Figure 10:
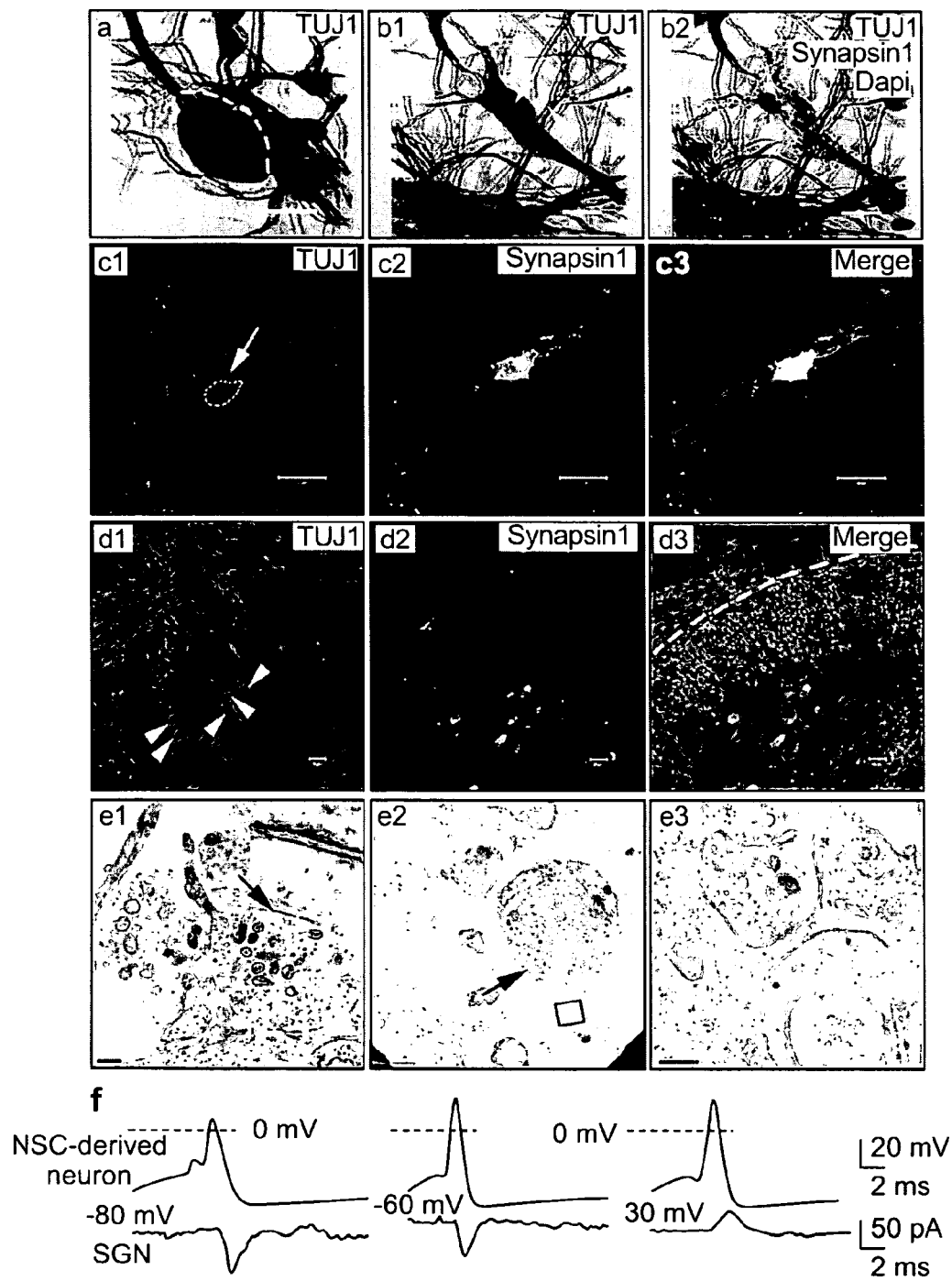
FIG. 10 shows NSC derived neurons functionally rewire deafferented SGNs. (A) SGN and NSC derived neurons were labeled with TUE. White dashed lines indicate a co-cultured adult SGN, which is about 4 times larger than a NSC-derived neuron (arrow). Various contacts were found between SGNs and NSC derived neurons. (B1) The nerve fibers of adult SGNs (arrow) were much thicker than that of NSC-derived neurons (arrowhead). (B2) Presynaptic protein synapsin 1 accumulated at the nerve endings of SGNs. (C1-3) Adendrosomatic-like contact between a large SGN nerve ending (arrow) and the cell body of a NSC-derived neuron (marked with white dashed line). Accumulations of synapsin 1 at the nerve ending of a SGN are shown. DAPI was used to show the nuclei. (D1-3) SGNs and NSC-derived neurons could also establish synapse-like contacts at the organ level. Adult NSCs were co-cultured with cochlear explants. Nerve fibers of NSC-derived neurons passed through the cochlea, integrating into the neuronal circuit of SGNs and establishing synapse-like contacts. The arrowhead indicates co-cultured SGNs (D1). The white dashed line marks the margin of the co-cultured cochlea. (E1) Ultra structure of a bouton from an adult NSC-derived neuron was filled with synaptic vesicles and the neuron was able to establish synaptic contacts with another adult NSC-derived neuron. The postsynaptic thickening (arrow) is enlarged at the upper right corner of this panel. (E2 and 3) The nerve ending of a NSC-derived neuron developed into a bouton with synaptic vesicles as it established a synapse with a SGN (arrow). The boxed area in panel (E2) is enlarged in panel (E3) to show the synaptic contact. (F) Functional analyses of synapses between SGNs and NSC derived neurons. Shown are examples of action potentials evoked from a NSC-derived neuron using negative current (~300 pA) injection. Below are simultaneous voltage-clamp recordings of synaptic currents from a SGN making synaptic contact with the NSC-derived cell. The magnitude of the synaptic current reduced as the SGN was held from −80 mV and −60 mV. In addition, the current reversed from negative to positive holding potentials. The mean synaptic delay was 0.6±0.3 ms; n=9. (Scale bars: A-D3, 20 µm; E1 and 3, 0.5 µm; E2, 5 µm.)

NSCs make functional synapse with target-deprived SGNs. This work determines whether NSC-derived neurons could establish functional synaptic connections with adult SGNs. To accomplish this NSCs were co-cultured with adult SGNs (FIG. 10). The SGNs and NSC derived neurons can be handily distinguished by their sizes; SGNs are ~4-fold larger than NSC-derived neurons (FIG. 10a). Dendo-dentritic synapses were formed.

Figure 11:
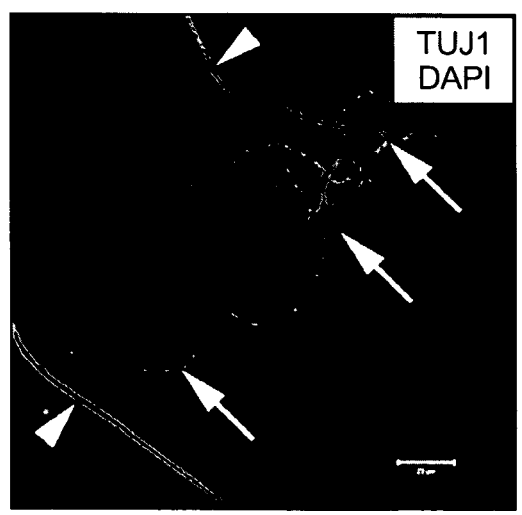
FIG. 11 is an example of NSC-derived neuron serving as an interneuron between SGNs. The neurite of a NSC derived neuron (arrows) projected to and linked the neurites of two deafferentated SGNs (arrowhead). (Scale bar, 20 µm.)

Additionally, NSC-derived neurons appeared to act as interneurons, linking the deafferentated SGNs (FIG. 11). The expression of synapsin 1 was invariably restricted to the axo-dendritic and axo-somatic contacts, suggesting that these may be genuine synapses (FIG. 10b1-c3). To test whether the synapse-like connections between SGNs and NSC-derived neurons could occur at the organ level, cochlear explants containing SGNs and NSC-derived neurons were co-cultured.

As shown in FIG. 10d1-d3, NSC-derived neurons extended their neurites through the cochlear explant to establish connections with SGNs. The corresponding expression of synapsin 1 at the site of contact between the two neuronal subtypes suggested the formation of synapses. An ultrastructural study showed characteristic membrane-associated density and synaptic thickening.

Moreover, a sizable proportion (85+6%; n=3) of the synapses were recognizable by other features, such as the apposition of the pre- and postsynaptic membranes, the presynaptic vesicle clusters and the specialization of the synaptic cleft (FIG. 10e1-e3). These analyses verified that the synapses formed between NSC-derived neurons and SGNs are equipped with the synaptic machinery to be functional.

From this baseline, electrophysiological analysis was employed to establish the operational status of synapses identified in vitro and to determine whether their properties are consistent with a bona-fide synapse, albeit in culture. Despite the prolonged culture conditions (7-9 days), NSC-derived neurons and adult SGNs were electrically healthy, with mean resting membrane potentials of (in mV)-49+6 and −56+5 (n=17), respectively. However, injection of positive current (1-50 pA) did not suffice to elicit action potentials in NSC-derived neurons.

Because cell culture conditions can greatly influence the functional expression of ionic channels, in particular the down regulation of inward rectifier $K_+$ currents that clamp the resting membrane voltage towards the $K_+$ equilibrium potential (~−80 mV) (32), the measured resting membrane potential was expected to have inactivated inward $Na_+$ and $Ca_{2+}$ currents that are responsible for the depolarization phase of action potentials. Predictably, injection of negative current to release the inward currents from inactivation resulted in the generation of robust action potentials. As illustrated in FIG. 10f, during dual recordings from NSC-derived neurons, that projected axons unto adult SGNs, elicited action potentials resulted in excitatory postsynaptic inward currents in the SGN. Analysis of the delays in synaptic events (0.6+0.3 ms; n=9) suggests that the synaptic activity may be mediated by a classic fast neurotransmitter. In 17 out of 26 dual recordings SGNs served as the postsynaptic neurons, whereas in the remaining 9 they operated as presynaptic neurons.

Discussion

This is the first extensive analyses using structural, molecular and functional criteria to demonstrate that adult brain germinal zone cells, derived from the same neuro-ectodermal layer as the otic vesicle epithelial cells, preserve the potential to undergo a functional switch to replace the non-renewable inner ear sensory cells, i.e., HCs and SGNs. Previous reports have demonstrated that the regenerative potential of HCs following damage is largely restricted to self-repair of stereo-cilary bundles (33, 34). Regenerative proliferation in inner ear sensory epithelia has been reported, but is limited due to the paucity of putative new HCs production (35). *Drosophila* atonal homologs, essential genes for inner HC development (36), have been used to stimulate HCs production from supporting cells (3, 23) and to provide modest improvements in the hearing function of guinea pigs (3). Overexpression of Math1 in postnatal rat cochlear explant cultures induces the production of extra HCs (23). Hes1 can negatively regulate hair cell differentiation by antagonizing Math1 (37, 38). It has been suggested that the sensory epithelia of the inner ear may be the only conducive niche for HC differentiation (2), however, the mechanisms underlying HC differentiation are so far not fully understood. Cell replacement therapy is one potential way to repopulate damaged HCs.

Pluripotent inner ear stem cells and transplanted exogenous progenitor cells have been verified as candidate cells (2, 6-8, 39), but the controlled differentiation of stem cells into functional HCs is essential for hearing restoration.

In the present study, evidence suggesting that ependymal cells of the LV have proliferative potential and that these cells have essential characteristics that liken them to HCs were provided.

They are polarized with actin-based stereocilia and microtubule-based kinocilia, can be identified by the well-characterized and commonly used HC markers (40) and express large conductance FM-143-permeable channels that are blocked by dihyrostreptomycin (26). Also notably important, cells of the ependymal layer have several of the defining electrophysiological characteristics of HCs: they are electrically active, send synaptic input to target-deprived SGNs and are capable of releasing glutamate in response to membrane depolarization. The identity of myosin VIIA-positive cells in the LV remains unclear, but they are not likely to be of neuronal or astrocytic origin, as they are essentially non-reactive to antibodies for neuronal and glial markers. Since the ependymal cells are sculpted with substantial components of HC phenotypes, Applicant believe that ependymal cells may undergo a functional switch to serve as hair-cells in the inner ear.

In inner ears, SGNs depend on neurotrophic factors released by HCs for survival (41). The ensuing degeneration of neurons following HC loss renders the need to replace or regenerate deafferented SGNs. In cases of primary SGN loss, auditory HCs remain intact, repopulation of lost SGNs with NSC-derived neurons may provide immediate improvement of hearing rehabilitation. Previous studies have attempted to replace lost SGNs by transplanting neurons from other ganglia or stem cells from exogenous sources, such as embryonic stem cells and neural stem cells (42, 43). None of these preliminary studies have demonstrated functional targeting to HCs. NSCs show extensive self-renewal capacity and differentiate spontaneously into neural cells. Transplantation studies have demonstrated the role of environmental factors in the fate decisions of adult NSCs. Adult NSCs differentiate into glia when transplanted into normeurogenic regions (e.g. spinal cord); however, they adopt a neuronal fate when transplanted into neurogenic niches (44). The mature inner ear is not an enriched environment for neuronal differentiation (42) and the transplantation of pre-differentiated NSCs is more likely to provide an effective functional replacement. These experiments demonstrate that, given favorable conditions, some NSCs from the SVZ of the LV (45) can develop into neurons with essential features of SGNs; they are bipolar neurons that form synapses with HCs. More importantly, they respond to synaptic inputs from HC and fire action potentials. These findings not only demonstrate that adult-derived stems cells retain biochemical and functional potentials akin to embryonic stem cells (46), they also reveal the immensely unknown potentials of NSCs in the auditory setting. In addition to neurotrophic factors, synaptic activities likely activate multiple pro-survival signaling pathways that regulate SGN survival and neurite growth (47). In this study, NSC-derived neurons form various types of synapses with SGNs and are capable of generating electrical activities, which may provide pro-survival signals to promote SGN survival and neurite growth and targeting.

To repopulate lost HCs in the auditory setting, ependymal cells can be introduced into the damaged inner ear, where they may reprogram their functions to replace lost HCs. Co-transplantation with NSCs from the same brain germinal zone may further facilitate the reconstitution of sensorineural circuits to achieve hearing restoration. The functional plasticity of renewable cells revealed in this study may open a new therapeutic avenue for other neural degenerative diseases.

Example 2

Adaptive Functional Switch: a New Stratagem for Repopulation of Non-Renewable Sensory Cells Methods Animal. All protocols used in this study adhered to NIH and Society for Neuroscience guidelines for care and use of animals in research. Every effort was made to minimize animal suffering and to reduce the number of animals used. The care and use of animals in this research were approved by the Ethical Committees at University of California in Davis. C57BL/6j mouse (8-12 weeks old,) ordered from Jackson.

Adult SGNs from adult mouse inner ear were cultured by methods known in the art and described in (60), incorporated herein by reference.

Reverse transcription-polymerase chain reaction (RT-PCR) Total RNA was extracted using RNeasy Mini Kit (Qiagen, Valencia, Calif.) from about 30 mg of the mouse choroid plexus tissues. RNA integrity was examined by agarose gel electrophoresis. The mRNA expression of different molecular markers was analyzed by RT-PCR. Briefly, first-strand cDNAs were synthesized from 1 μg of total RNA using T24 oligo dT primers (Ambion, Austin, Tex.) and SuperScript III reverse transcriptase according to the manufacturer's instruction (Invitrogen, Carlsbad, Calif.). PCR amplification was then performed with specific primer pairs at the optimized annealing temperatures for each primer pair (Table 1). To minimize DNA contamination, the primers used were designed to span at least one intron of the genomic sequence. In addition, all PCR were conducted on the same plate with a gradient cycle format using a mastercycler gradient (Eppendorf North America, Westbury, N.Y.); a ten-minute predenature at 94° C. followed by 35 cycles of amplification (94° C., 30 s; the optimized individual annealing temperature, 30 s; 72° C., 1 min). The fidelity of each RT-PCR product was verified by comparing it to the expected cDNA size and by sequencing the PCR product.

Immunofluorescence. Cultures were fixed with 4% paraformaldehyde in phosphate-buffered saline (PBS) for 20 minutes at room temperature, rinsed, and then pre-incubated for 60 minutes at 37° C. in blocking solution (3% bovine serum albumin, 0.3% Triton X-100 in 0.1 M PBS). Blocking solution with 50% (v/v) normal goat serum added was applied at 37° C. for 30 minutes, and cultures were then incubated with different primary antibody combinations (diluted in blocking solution) at 4° C. for 12 hours. The following primary antibodies were used: mouse anti-β tubulin III (Tuj1) (BAbco, 1:700), mouse anti-synapsin1 (SY SY 1:1000), rabbit anti-β tubulin III (BAbco, 1:2000), mouse anti-O4 (Chemicon, IgM, 1:100), rabbit anti-glial fibrillary acidic protein (DAKO Cytomation, 1:1000). After discarding the primary antibody solution, the slides were rinsed 3 times in PBS, and incubated with secondary antibodies: Cy3-conjugated goat anti-mouse IgG, Fcγ fragment (Jackson ImmunoResearch, West Grove, Pa., 1:1600), Cy5-conjugated goat anti-mouse IgG (Jackson ImmunoResearch, 1:1200), Cy3-conjugated goat anti-rabbit IgG (Jackson ImmunoResearch, 1:1200) and Alexa488-conjugated goat anti-rabbit (Molecular Probes, Eugene, Oreg., 1:1600), secondary antibodies were incubated for 90 minutes at room temperature. The slides were rinsed with PBS, incubated with 300 nM DAPI (4',6-diamidino-2-phenylindole, dihydrochloride) solution (Molecular Probes) for 5 minutes, and finally rinsed and mounted in anti-fading medium (P-7481, Molecular Probes). A Zeiss LSM 510 Meta confocal microscope or an Olympus fluorescent microscope equipped with a digital camera was used to collect images. Imaris Bitplane was applied for 3-D reconstruction of confocal Z-stack images.

In Vivo and in vitro proliferation of choroid plexus cells. For in vivo proliferation test, BrdU (100 mg/kg in 0.9% NaCl) was injected intraperitonealy once a day for 4 weeks prior to sacrifice. For visualization of BrdU-retaining cells, the whole brain was isolated and processed for cryosection, Myosin VIIA and BrdU staining was applied to the cryosections. For in vitro proliferation test, BrdU was added to the CP epithelial cell culture medium 48 hours after initial culture.

Cryosection of mouse brain and choroid plexus. Brains were collected from untreated male and female C57BL/6 mice (8-10 weeks old, Charles River). After decapitation, brains were collected and wrapped with aluminum foil, then flash-frozen with dry ice.

Assay for mechanosensory transduction in CP epithelial cells: The animal was sacrificed by cervical dislocation then the choroid plexus of the lateral ventricle was exposed to 5 μM FM1-43FX (Molecular probes) for 60 seconds and fixed with 4% formaldehyde. The thin piece of choroid plexus was mounted to examine the fluorescent intensity to determine dye uptake. To block the entry of FM1-43, the lateral ventricle was pre-incubated and repeatedly flushed with DHS for 4 minutes.

Electrophysiology. Hair cells were identified by the presence of green fluorescence under ultraviolet light. Neural stem cell originated neurons were identified by their distinct neuronal morphology (small, round and phase bright cell body and long uneven processes), spiral ganglion neurons were identified by their much larger round and phase bright cell bodies and unipolar and/or bipolar neurites. The criteria were confirmed by immunostaining in parallel cultures. CNQX (10 μM) was used to block AMPA receptors.

Transmission electron microscopy (SEM) Mice were sacrificed by cervical dislocation, lateral wall of lateral ventricle were dissected, fixed with 2.5% glutaraldehyde and 2% paraformaldehyde. For SEM, samples were dehydrated, final dried and infiltrated with gradient Hexamethyldisilazane, mounted and coated with gold. Images were collected on an Philips FEI XL30 SEM. For TEM, samples were post-fixed in 1% osmium tetroxide, dehydrated, infiltrated and polymerized. Ultrathin sections were post-stained. Images were taken on a Philips EM400 TEM with a MegaView digital camera (Soft Imaging Systems, Inc).

Results

Several types of cells including exogenous stem cells have been tested to serve as potential sources for replacement of damaged inner ear HCs (51, 56, 58, 59), however, the production of new HCs is either a rare event, or a controlled differentiation is needed to generate functional HCs from these cells. Here a new strategy of HC replacement therapy is described; other renewable neural epithelia-derived cells which possess considerable similarities with HCs may reprogram their functions to carry out mechanoelectrical transduction in damaged inner ear, thus serve to accomplish hearing restoration.

Figure 12:
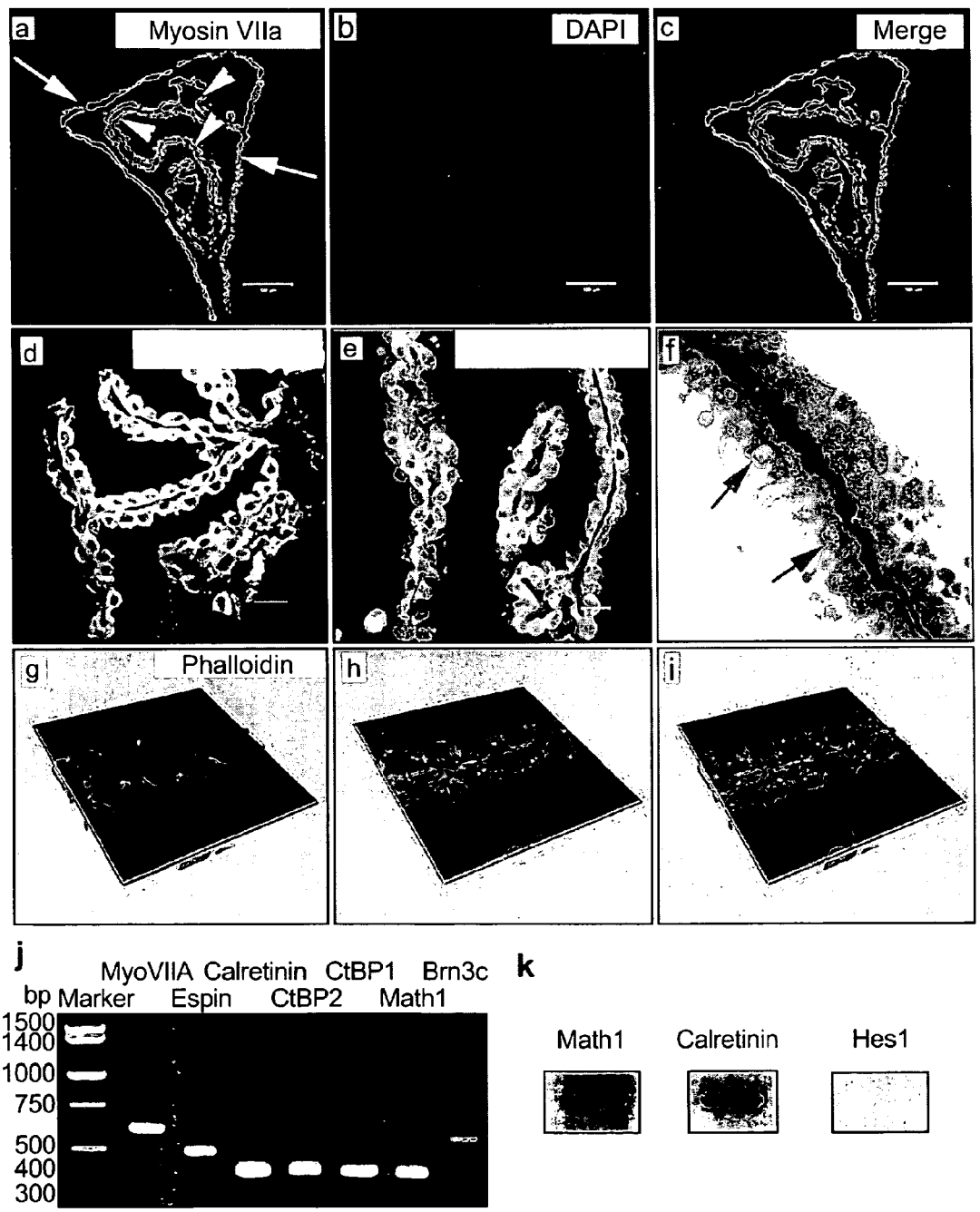
FIG. 12 shows expression of Myosin VIIA in choroid plexus (CP) epithelial cells (12a-d).

In this study, it was demonstrated that choroid plexus (CP) epithelial cells share essential morphological and functional characteristics with inner ear HCs. CP is covered by a monolayer of ependymal-derived, cuboid epithelial cells, which is derived from the primordial neuroepithelium of the neural tube. It is shown in Example 1 that Myosin VIIA, a specific structure protein of inner ear hair cells, which is required for structural integrity of hair bundles and important for hearing (57, 61), specifically expressed in brain ependymal cells. Here, the expression of Myosin VIIA in CP epithelial cells (FIG. 12a-d) was demonstrated. Meanwhile, myosin VI, another specific structure protein of inner ear hair cells also expressed in CP epithelial cells (FIG. 12e). Accordingly, CP cells take the shape of polarized columnar epithelial cells with enriched stereocilia-like microvilli localized on top of them (FIG. 12f-i). Expression of additional HC related molecules also have been detected at RNA level (FIG. 12j) and some of them have been detected at protein level. In addition to the expression of specific hair cell markers, the CP cells were also characterized by the absence of inner-ear supporting cell marker Hes1 (FIG. 12k).

Since HC cell's signature characteristic is sensing mechanical stimuli, the key issue of this proposed cell replacement therapy is: whether the CP epithelial cells are equipped with mechanical-sensitive apparatus and how well they can respond to mechanical stimuli? In this study, the uptake of FM1-43 (FIGS. 13a1,13a2) was first observed in CP epithelial cells, with the same pattern as in mechanosensory cells, indicating existence of mechanotransduction channels in these cells (54). And, the uptake of FM1-43 was inhibited by dihydrostreptomycin (DHS), an aminoglycoside antibiotics use the same entry pathway in hair cells (FIGS. 13b1, 13b2). Most importantly, when vibrations with different frequency were applied onto the stereocilia-like structures of CP epithelial cells, the introduced mechanical stimuli evoked similar characteristic electrophysiological response in CP epithelial cells as HCs respond to the sound wave-induced vibration (FIG. 13c).

Figure 13:
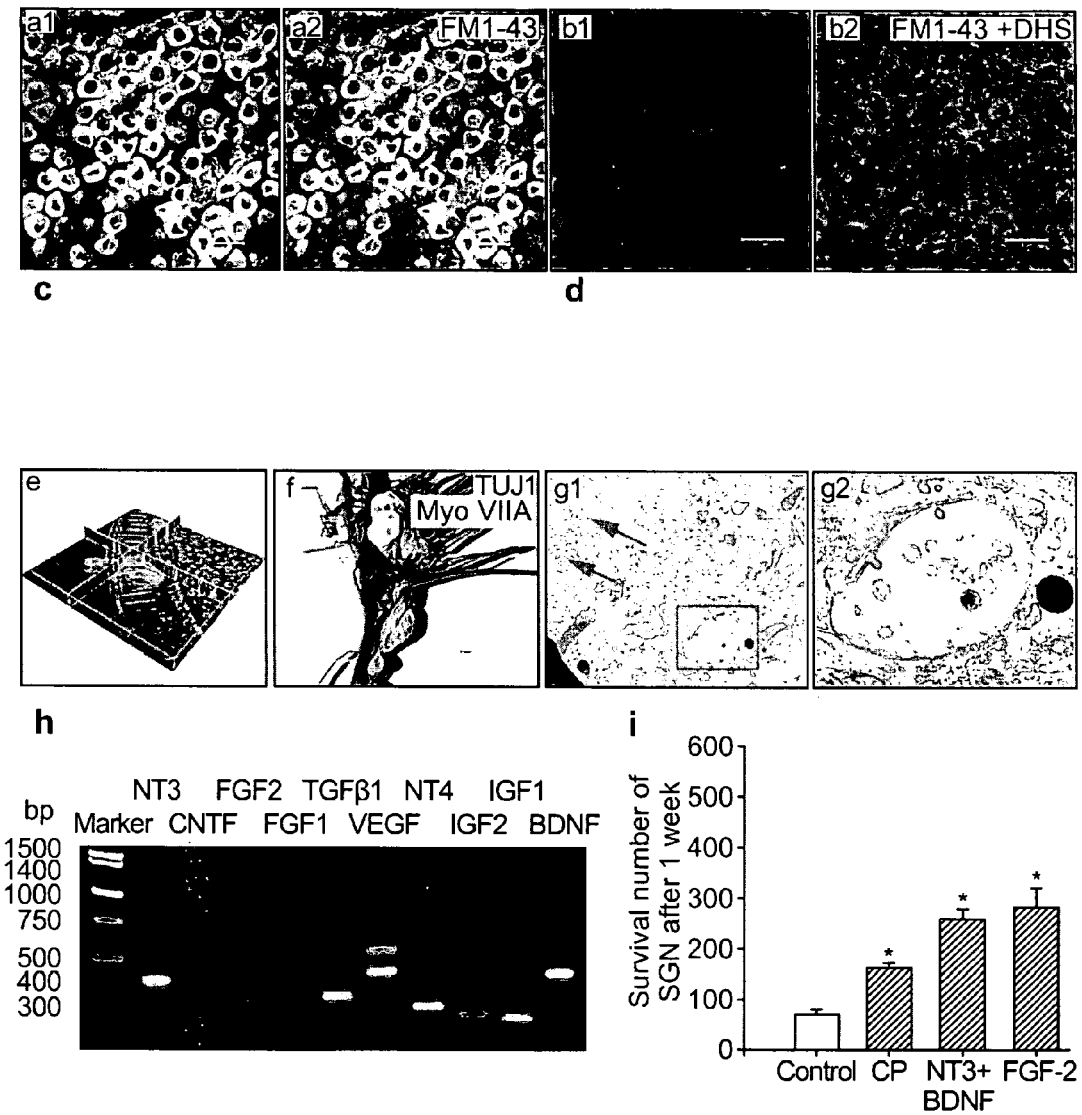
Figure 14:
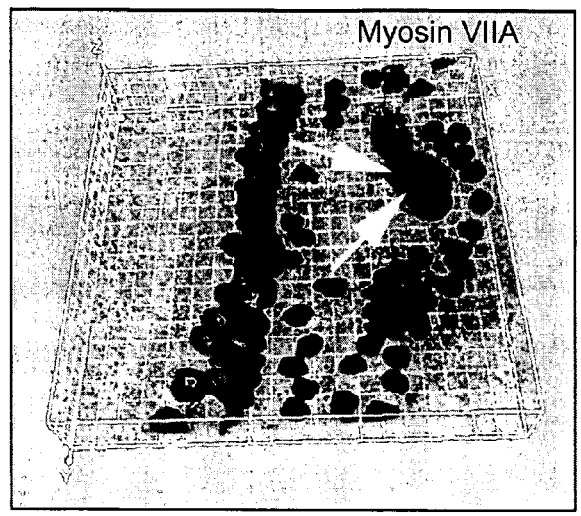
FIG. 14 shows that CP could incorporate into the intact cochlear sensory epithelium with full set of HCs.

If they are to fulfill their promise as a replacement of HCs, it is important that the CP epithelial cells can integrate into the inner ear sensory circuit and functionally couple with the deafferentated SGNs. As shown in FIG. 13, CP epithelial cells could blend into the co-cultured cochlear sensory epithelia (FIG. 13e), where HCs were already picked-off to mimic the primary HC loss. Interestingly, CP could incorporate into the intact cochlear sensory epithelium with full set of HCs as well (FIG. 14). To verify the possibility for the CP epithelial cells to establish functional connections with SGNs, CP were co-cultered with deafferentated SGNs. As revealed in FIG. 13f, some of the regenerated neurites recognized CP epithelial cells as their targets and arborized to innervate them. Transmission electron microcopy detected synaptic structure between coupled CP-SGN (FIG. 13g). Furthermore, the mechanical stimulations exerted on CP epithelial cells elicited corresponding synaptic responses at their coupled SGNs (FIG. 13d), the fact that these synaptic responses were sensitive to a glutamate receptor blocker, CNQX (FIG. 13d), gives further credence to the functionality.

The unattended primary HC death will eventually lead to secondary degeneration of SGNs due to lose of survival promoting stimuli. Infusion of neurotrophic factors into inner ear is proved effective to save SGNs after HC death. Growing evidences have indicated that CP is a major site of synthesis of a large number of growth factors and neurotrophins and is closely involved in neuronal repairing and protecting processes (49, 50, 55, 53). Interestingly, some of these factors are the same supporting molecules released from HCs to maintain SGNs. the reasonable presumption is: can CP serve as a source of trophic factors to preserve SGNs as HCs do? In this study, using reverse transcription-polymerase chain reaction (RT-PCR), active transcription of various neurotrophic factors in CP epithelial cells was detected (FIG. 13h). Meanwhile, when co-cultured with isolated SGNS, CP epithelial cells demonstrated a significant neural protective effect on SGNs, with comparable level as conferred by synthesized neurotrophic factors (FIG. 13i).

Figure 15:
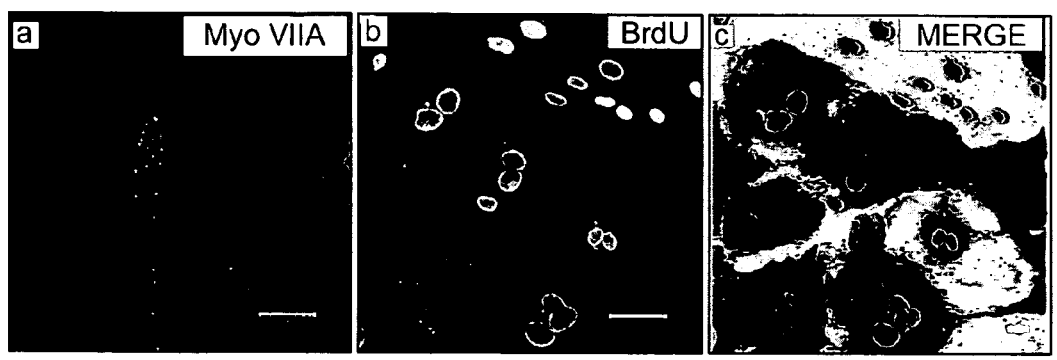
FIG. 15 shows that the normally quiescent CP epithelium cells demonstrated an active proliferation upon stimulation with mitogens.

It is worth to address that the normally quiescent CP epithelium cells demonstrated an active proliferation upon stimulation with mitogens (FIG. 15). The capacity of re-entering cell cycle and reproduce themselves renders the CP epithelial cells further fulfilling the criteria as a novel resource to repopulate the non-renewable HCs.

Hearing restoration is based on HC repopulation and preservation of SGN. Applicants identified CP epithelial cells as a novel potential substitution of HCs via the mechanism of adaptive functional switch and achieve the signature performance of HCs. Without being bound by theory, understanding of the mechanisms of this functional plasticity may give rise to a new cell replacement strategy: renewable cells derived from the same germ layer may fill the vacancy of nonrenewable-highly differentiated cells by reprogramming their functions to adapt the new environment. Meanwhile since SGN preservation is another major concern of hearing rehabilitation. Stable secretion of neuroprotective cocktail, escaping immune rejection by autologous transplantation and tolerance of immunosuppressant treatments (52), make CP cells the appealing choice for SGN preservation. This neuroprotective capability of CP may extend to design novel therapeutic facilities targeting neurodegenerative diseases.

Example 3

Methods of Isolating Ependymal Cells and Choroid Plexuses

Isolation and culture of mouse ependymal cells. The thin layer of lateral wall of lateral ventricle was dissected out, and dissociated with an enzyme cocktail: (0.7 mg/ml hyaluronase, 1× trypsin-EDTA, and 200 U/ml DNaseI), after trituration, mixed with same volume of 4% BSA. Cell solution was filtered through a 40 µm cell strainer and centrifuged. Cell pellet was re-suspended in D-MEM/F-12 with GlutaMAXTM1 (Invitrogen) supplemented with B27 (Invitrogen) and cocultured with spiral ganglion neurons. The culture dish was kept in incubator at 37° C. with 5% $CO_2$ in a humid environment.

Isolation and culture of mouse choroid plexus. Animals were killed by cervical dislocation, brains were quickly dissected in an ice-cold dissecting solution consisting of Minimum Essential Medium with Hanks' salts (Invitrogen), 0.2 mg/ml kynurenic acid (Sigma), 10 mM $MgCl_2$, 2% FBS (v/v), and glucose (6 g/l). The choroid plexuses were harvested from lateral ventricle, then digested in an 37° C. enzyme cocktail containing collagenase/dispase (1 mg/ml, Roche). Enzyme solution was identical with dissecting solution except that 2% FBS was replaced with 2% B27. After 20 minutes of incubation, trypsin (2.5 mg/ml, Invitrogen) was added to enzyme solution to make a final concentration of 0.25% and kept digested at 37° C. for 10 minutes, FBS was applied to 50% (v/v), digested tissue was gently triturated, cell solution was spinned for 10 minutes at 700×g. Cell pellet was re-suspended in D-MEM/F-12 with GlutaMAXTM1 (Invitrogen) supplemented with B27 (Invitrogen) and cocultured with spiral ganglion neurons.

Example 4

Hearing Restoration by Adaptive Functional Switch

Several types of cells including exogenous stem cells have been tested to serve as potential sources for replacement of damaged inner ear. However, the production of new HCs is either a rare event, or a further differentiation manipulation is needed to generate functional HCs from these cells. In this study, Applicants demonstrate that choroid plexus (CP) epithelial cells share essential structural and functional similarities with inner ear HCs, terminally differentiated CP cell is capable of both functional replacement of HCs and preservation of SGNs. Applicants thus propose a new strategy of cell replacement therapy: other renewable neural epithelia-derived cells may adjust their functions to carry out the key function of medically important but nonrenewable neuroepithelial cell types to repair diseased or damaged tissues.

Morphologically, CP is covered by a monolayer of ependymal-derived, cuboid epithelial cells. Applicants have shown in a previous study that Myosin VIIA, a specific structure protein of inner ear HCs, which is required for structural integrity of hair bundles and important for hearing (57, 72), specifically expressed in brain ependymal cells (71). Here, Applicants demonstrate that the CP epithelial cells also carry this featured protein. Meanwhile, prestin and myosin VI, another two specific structure protein of inner ear HCs also expressed in CP epithelial cells. Accordingly, at the ultrastructural level, the CP cells display the hallmark of HCs: CP cells take the shape of polarized columnar epithelial cells with enriched stereocilia-like microvilli localized on the apical surface.

Further assay on molecular similarities revealed that CP cells co-express genes essential for HC identity including Myo7a, Myo6, Math1, Espn, Brn3c, Ctbp2. Additional HC function related channel markers like α-1D, BK, SK2 also have been detected at RNA level and some of them have been detected at protein level. To confirm the CP cells do not exhibit a hybrid or mixed characteristics, Applicants have also demonstrated that CP cells are absent of inner-ear supporting cell marker Hest.

The good overlap of principal HCs genes and proteins on CP cells, suggests that CP cells may serve as a good alternative, which is already well equipped with essential HC configuration.

Since HC cell's signature function is sensing mechanical stimuli, the key issue of this proposed cell replacement therapy is whether the CP epithelial cells carry mechanical-sensitive apparatus and how well they can respond to mechanical stimulation? Although, the lack of convincing evidence for HC specific mechanotransduction channel makes the molecular fingerprint identification of this channel in CP cells currently unavailable. However, CP cells stood a comprehensive proof testing of the functional fingerprint.

Applicants first observed the uptake of FM1-43 in CP epithelial cells, with the same pattern as in mechanosensory cells, indicating existence of mechanotransduction channels in these cells (34). Interestingly, the uptake of FM1-43 by CP cell was bloked by dihydrostreptomycin (DHS), an aminoglycoside antibiotics use the same entry pathway in hair cells. Most importantly, when Applicants applied vibrations with different frequency onto the stereocilia-like structures of CP epithelial cells, the introduced mechanical stimuli evoked similar characteristic electrophysiological responses in CP epithelial cells as HCs respond to the sound wave-induced vibration. These data show that the HC like CP cells are capable of mechano-sensation.

To serve as an effective substitute, CP cells should be recognized by SGNs and are capable of delivering mechano-electrical transduction to SGNs. Applicants thus asked whether the CP epithelial cells could establish functional connections with SGNs, Applicants co-cultured them with deafferentated SGNs. Some of the regenerated neurites recognized CP epithelial cells as their targets and arborized to innervate them. Robust staining of synapsin 1 at the sites of contact suggests that connections between SGNs and CP cells may form synapses. Transmission electron microcopy detected synaptic structure between coupled CP-SGN. Furthermore, the mechanical stimulations applied on CP epithelial cells evoked active mechnoelectrical transductions and elicited corresponding synaptic responses at their coupled SGNs (FIG. 2d), the fact that these synaptic responses were sensitive to a glutamate receptor blocker, CNQX, gives further credence to the functionality. This result is encouraging because it shows that functional synaptogenesis between CP epithelial cells and deafferentated SGNs is possible after regrowth of neuronal processes Substitutive cells only armed with featured HC structures do not guarantee hearing recovery, additional request for effective HC replacement therapy is: the candidate cells should be able to release neurotrophic factors, otherwise the secondary degeneration of SGNs is inevitable due to lose of neurotrophic supports from their primary target cells. The reasonable presumption is: can CP serve as a source of trophic factors to preserve SGNs as HCs do? Growing evidences have indicated that CP is a major site of synthesis of a large number of growth factors and neurotrophins and is closely involved in neuronal repairing and protecting processes (49, 50, 53 and 55). Interestingly, some of these factors are the same supporting molecules released from HCs to maintain SGNs. When co-cultured with isolated SGNs, CP cells demonstrated a significant neural protective effect on SGNs, with comparable efficacy as conferred by synthesized neurotrophic factors. The endogenous secretion of SGN protective factors from CP avoiding the conventional molecular and genetic manipulation to release selected neurotrophins raised their credibility as an HC replacement.

Applicants next asked whether the terminally differentiated CP cells could re-enter cell cycle and reproduce themselves, which is one of the most important criteria for cell replacement therapy. Notably, Applicants have observed the normally quiescent CP epithelial cells demonstrated an active proliferation capacity upon stimulation with mitogens. This capacity renders the CP epithelial cells to repopulate the non-renewable HCs. As a potential resource of autologous implants, CP may provide fresh opinions to autologous transplantation, which has long been believed not practical for therapeutic purposes, because the tested cells are restricted to the type of their original tissue and generally have limited proliferative potential (70).

Another key issue that needs to be addressed is whether this self-reproducible and functional viable CP cells could integrate into the inner ear sensory circuit. Applicants have shown that CP epithelial cells could integrate into the co-cultured cochlear sensory epithelia, where HCs were already picked-off to mimic the primary HC loss. Interestingly, CP could incorporate into the intact cochlear sensory epithelium with full set of HCs as well. The successful integration of CP cells into organ of Corti reveal their defining feature of breaking tight junctions and other cellular connections at the apical side of the sensory organ.

Applicants' in vitro studies specified that CP epithelial cell could be a good substitute of nonrenewable inner ear HCs, which has satisfied numerous criteria to behave like a functional HC. The promising in vitro data prompts the in vivo animal model to evaluate the possible efficacy using CP cells as a novel stratagem for hearing restoration.

Although endogenous stem cells are present in mature inner ear sensory epithelia and in spiral ganglion tissue (2, 5, and 66) and are capable of giving rise to HCs and SGNs, however, active regeneration may not occur due to decline of stem cell population after birth (67) and physiological environment is not optimal for active regeneration. Therefore, cell transplantation may be the appropriate option for hearing rehabilitation.

However, hearing recovery via transplantation of donor cells into mature inner ear is fastidious, although Applicants proposed stratagem skipped the great difficulties in achieving HC differentiation, however, numerous challenges remains to be addressed: selection of optimal injection site to minimize tissue damage while to place donor cells as close as possible to the target site. The timing of transplantation? Can grafted CP cells recovered from a high potassium environment where native HCs reside? Are CP epithelial cells mechanically and structurally compliant with the native tissue? Can CP cells access the functional important sites? Correct interaction with proper host cells?

An essential request of cell replacement therapy is to deliver the potentially restorative cells to the target, usually the site of the lesion. Applicants, therefore, choose the scala media as the injection site, because this area is more functionally appropriate for implanted CP cells to replace HCs. Previous studies on the mechanical compliance of this chamber have shown that injection of artificial endolymph at the delivery rate<500 nl/minute was thought to have little or no mechanical influence in the inner ear (63), in this study Applicants did not find significant trauma and the rupture of membranous labyrinth.

As for the timing of transplantation, Applicants have seen that damaged inner ear sensory epithelia may provide a more permissible environment for donor cells than uninjured tissue. Applicants then injected donor CP cells after deafening of adult rats.

Applicants' in vivo investigation also proved the survival of CP cells at high potassium environment: small numbers of survived CP cells were observed attached to multiple cytoarchitecture within pre-deafened cochlea at least 4 weeks following transplantation: the scala media, the scala vestibuli, the scala tympani, and also in the modiolus. The transplanted CP cells did not just stay at the point of injection; they were capable of reaching the whole expanse of the cochlear scalae definitely wider than was expeceted. No visible inflammatory tissue response was observed. The presence of transplanted CP cells in the extra-scala media sites was most likely due to mis-delivery to these regions during the surgical procedure. This mis-delivery is difficult to avoid given the tiny size of the scala media. Another possibility is: the transplanted CP cells could have migrated to multiple areas from the scala media.

To distinguish implanted CP cells from the host cells, Applicants used CP cells from mice expressing an enhanced green fluorescent protein (EGFP) transgene driven by a Myo7A promoter. The lack of GFP identity in implanted CP cells could be attributable to the effects of the two-week decalcification period (BioTechniques (2002) 33:1197-1200). To confirm the ectopic myosin VIIA positive cells were of mouse origin, the grafted CP cells were identified by myosin VIIA and a mouse-specific antibody double staining.

Even though a significant decline in the number of surviving CP cells was noticed which indicated a low survival rate in the scala media, however, this result was still promising, because it established the survival potential of CP cells within this harsh but physiologically important site, albeit in small numbers. The fact that CP cells get settled at the normal location of HCs means a significant step-forward toward the functional replacement of HCs. Nonetheless, the predominant location of grafted CP cells at the extra-scaca media area suggests that the high potassium concentration was less preferable for the survival of CP cells.

It is generally believed that effective replacement of HCs with grafted cells is difficult due to the poor functional integration. In this study, integration of the transplanted CP cells into the functionally important site of the cochlear sensory circuit was observed.

This mechanic-resonsive HC-like cell also demonstrated structural compliance with the native sensory circuit by integrating into Rosenthal's canal (RC), the site of residual deafferentated SGNs, and exhibited efficacious improvements in hearing thresholds.

A small number of CP cells were detected within RC and in close proximity to surviving SGNs. Other implanted cells also had been observed at this site (Cell Transplant. (2006) 15(5): 369-380). The possible route through which the transplanted CP cells reached the RC is: habenula perforate, the site where auditory nerve fibers emerge from RC into the scala media. Under normal circumstances, habenula perforate was tightly occupied by the passenger SGN fibers and leave no available space for the passage of grafted CP cells. However, the secondary degeneration of SGNs following the death of HCs will lead to missing and/or degeneration of SGN fibers, which will create enough space in the habenula perforate for transplanted cells to pass through. The atrophic nerve fiber themselves may serve both as the guiding path and as sites of rescue signals that facilitate CP cell migration. Although transplanted CP cells detected within Rosenthal's canal did not occur in great numbers, but this finding indicates a privileged homing location that is well-suited for capturing afferent fibers from SGNs: the target-hunting appears much easier along this defined anatomical route. The attractant cues from both degenerating SGNs and from CP cells may help to wire them together and achieve hearing recovery.

The possible explanations for integration of CP cells into the sensory epithelia is, firstly, exposure to neomycin led to HC death and related disruption of the barrier at the luminal surface of cochlear sensory epithelia caused by aminoglycoside ototoxicity (64). Applicants' microscopy data also revealed a dynamic structural remodeling of cochlear sensory epithelia immediately after neomycin induced HC loss, which suggest a reasonable time window for implantation and integration. Secondly, CP cells are reported as a source of enzymes that catalyze the cleavage of basal lamina components, tight juctions (62, 65 and 73) and thus are involved in the remodeling of the cytoarchetecture and in cellular migration. Exposure to an inflammatory-like environment leads to an increase in this tissue-lytic enzyme secretion (68). Pre-deafening with neomycin may create a viable environment for CP cells to break down the tight junction barriers which normally prevent the integration of donor cells into organ of Corti. However, the extracellular structural matrix of organ of Corti could be an impediment for CP cells attachement. Feasible approaches that may create appropriate extracellular microenvironments for cell attachment should be considered.

Another explanation of CP cells integrating into multiple sites of cochlea is: remodeling of host tissue, i.e., graft-induced host plasticity). Grafted CP cells may modify the local environment to create an enriched environment for their survival.

Applicants suggest that the cellular functions associated with integration are not expressed constitutively by grafted cells, the instructive signals released from local microenvironment are also critical.

Neurite outgrowth from the surviving SGNs toward integrated CP cells was also observed. Meanwhile, the morphological switch of the implanted CP cells is also noticed, some of them had adopted the morphologic phenotypes of outer or inner HCs.

The most critical judgment of this cell replacement therapy is evaluation of auditory input function, which identifies the real-time interaction between implanted CP cells and host auditory sensory cells. Interestingly, the introduction of a large number of CP cells into scala media did not appear to add additional significant adverse effects on the auditory input function. On the other hand, functional analysis of transplanted animals revealed hearing threshold improvement, suggested the rebuilding of the functional circuit. This result is in consistent with the cell integration demonstrated by histological examination.

Functional assessments revealed noticeable improvements in hearing thresholds, Applicants, thus, have demonstrated a measurable functional recovery of transplanted CP cells. However, clinically significant recovery is still a major challenge that will require further experimentation with a range of different types and preparations of donor cells.

Applicants evaluated the functionality of cochleae that received CP transplants and control normal saline injected cochleae in deafened rats by measurements of auditory brain stem response (ABR), broadband clicks and pure tones (8, 16, and 32 kHz) were presented in the operated ear in 10 dB increments, starting from 0 dB sound pressure level (SPL) and ending at 100 dB SPL. Alterations in ABR thresholds between pre- and 1 week, 2 weeks, 3 weeks and 4 weeks post-operation were analyzed. The apparent down-shift of thresholds in transplanted cochleae than those in normal saline injected cochleae indicated a measurable function recovery after CP transplantation. This auditory acuity improvement may not be great enough to achieve a clinical standard, however, it is reasonable to believe that functional connections between implanted CP cells and the limited number of surviving SGNs may have been established, an essential request for implanted CP cells to improve the signal input function of the host auditory system. Alternatively, the remarkable hearing threshold down-shift by CP transplantation could be explained, at least in part, by the enhanced neurotrophic factor production, the additive neuroprotective effects were appreciated in the organ level of hearing measurement.

Discussion

Hearing restoration is based on repopulation of vibration sensitive cells and preservation of SGN. Applicants identified CP epithelial cells as a potential novel substitution of HCs which exhibit the principal characters of HCs via the mechanism of functional adaptation. The beneficial neuroprotective effects attached to CP cells indicate the feasibility and efficacy of this therapeutic strategy. Understanding the mechanisms of this functional re-patterning may give rise to a new cell replacement strategy: instead of lineage switch, the vacancy of nonrenewable functional important cells could be filled by lineage related renewable cells derived from the same germinal layer, the close relatives could achieve functional replacement via reprogramming their functions to adapt the new environment.

Although the richness and complexity of this functional plasticity remains to be appreciated, an updated concept of essential multipotency of lineage phenotypes should be broadened to include the emerging recognition of multi-functional potential.

Autologous transplantation has already achieved regulatory approval and reached the market for patients. These successful applications highlight the ongoing efforts to identify new autologous cell-based therapies. The recent advances in reprogramming of mammalian cells with defined transcription factors raise the possibility of generating patient-specific embryonic stem cells for therapies (67 and 74); however, this is a multiple-step process that requires specific manipulation of the iPS cells to produce therapeutically important cell types. In principle, patient-specific cell therapies could be achieved more directly by stratagems proposed in this study.

Meanwhile since SGN preservation is another major concern of hearing rehabilitation. The inborn capacity of secreting neuroprotective cocktail, escaping immune rejection by autologous transplantation and tolerance of immunosuppressant treatments (52), makes CP cells the appealing choice for SGN preservation. This neuroprotective capability of CP may extend to design novel therapeutic facilities targeting neurodegenerative diseases.

Experiment No. 4 Isolation and Use of Choroid Plexus Cells

Animals. All protocols used in this study adhered to NIH and Society for Neuroscience guidelines for care and use of animals in research. Every effort was made to minimize animal suffering and to reduce the number of animals. The care and use of animals in this research were approved by the Ethical Committees at University of California in Davis, C57BL/6j mouse (8-12 weeks old,) ordered from Jackson.

Culture of adult SGNs from adult mouse inner ear as previously described in Wei et al. (5).

Isolation of choroid plexus. Choroid plexus cells were isolated from myosin VIIA-GFP mice, p3-p7 days of age. Animals were killed by decapitation, choroid plexus tissue was quickly dissected from the lateral ventricle of the brain in an ice-cold dissecting solution consisting of Minimum Essential Medium with Hank's salts (Invitrogen), 2% B27, 1% N2 (v/v), and glucose (6 g/L).

The choroid plexus was digested in an enzyme cocktail containing collagenase-dispase (Roche), DNase I (Roche, 1 mg/mL) at 370 C for 20 minutes, then trypsin (Invitrogen) was added to make a final concentration of 0.25%. After incubation for 10 min at 37° C., addition of 50% (v/v) FBS, and gentle trituration, the cell solution was centrifuged for 10 min at 700 g. Cell pellet was reconstituted with dissecting solution and used for subsequent transplantation procedures.

Deafening protocol. The inner ear sensory cells of SD rats were deafened by an injection of 20% neomycin through the tympanic membrane. The middle ear cavity was filled with the neomycin solution, and the head of the animal was kept for 60 min in the operation-side-up position for the drug to diffuse via the round window membrane into the cochlea. This procedure generally causes considerable loss of the sensory cells, a subsequent injection of 20% neomycin was performed to the animals that did not show significant hearing loss. The animals were allowed to recover for 2-3 weeks to confirm no hearing recovery is in process, then the deafened animals were operated for CP cell implantation.

Transplantation of choroid plexus cells to scala media. Access to the rat inner ear is accomplished via a caudal-ventral approach. The animal is anesthestized with ketamine at 40 mg/kg body weight in combination with xylazine at 10 mg/kg body weight. Adequate anesthesia is assessed with foot pinch. Additional anesthetic is administered at doses of 10 mg/kg ketamine and 2.5 mg/kg versed at intervals as needed to ensure adequate anesthesia.

The skin 2 cm caudal and ventral to the auricle is depilated and sterily prepared with betadine solution. An incision is made and extended in the skin posterior and inferior to the auricle. The underlying superficial musculoaponeurotic layer is divided to expose the deep craniocervical musculature and parotid gland. The parotid gland is retracted anteriorly, and the occipitocervical and sternocleidomastoid muscles are divided. Mastoid periosteum is incised and elevated, and the underlying bulla is exposed.

The bulla is opened along the ventral plane and widened dorsally to the cranial base and rostrally to the bony annulus of the external auditory canal, taking care to avoid entering either structure. Sufficient resection of the bulla allows for wide exposure of the middle ear space and direct visualization of the cochlear promontory, round window niche, stapedial artery, stapes, and portions of the ossicular chain. This view is sufficient for obtaining intracochlear access via cochleostomy through the promontory and lateral wal into the scala media.

Cochleostomy is performed through the promontory bone and lateral wall of the first cochlear turn. The lateral wall is identified as the region of dark transverse striping along the promontory. A tuberculin syringe prefilled with experimental or control solution is attached to a small needle, which is used to perform the lateral wall cochleostomy. Following puncture through the bony wall, the needle is advanced through the lateral wall and 10-20 µL of preloaded solution (104/µl) slowly instilled into the scala media. The needle is withdrawn, and the cochleostomy is quickly sealed with bone wax in a watertight fashion.

The musculature overlying the bulla is brought together and closed with suture, and the wound is closed deeply and superficially with additional suture. The incision is dressed with antibiotic ointment, and the animal is recovered.

Histological Processing and cryosection of cochlea and brain. Animals were transcardiac perfused with either 4% paraformaldehyde in PBS. The cochlea and brain was isolated and postfixed overnight. Cochleas were then decalcified in 10% EDTA at 4° C. for 2 weeks. Cochleas and brains were processed sequentially with 10% and 30% sucrose at 4° C. overnight then embedded in OTC for cryosectioning.

Immunofluorescence. Cultures or sections were fixed with 4% paraformaldehyde in phosphate-buffered saline (PBS) for 20 minutes at room temperature, rinsed, and then pre-incubated for 60 minutes at 37° C. in blocking solution (3% bovine serum albumin, 0.3% Triton X-100 in 0.1 M PBS). Blocking solution with 50% (v/v) normal goat serum added was applied at 37° C. for 30 minutes, and cultures were then incubated with different primary antibody combinations (diluted in blocking solution) at 4° C. for 12 hours. The following primary antibodies were used: mouse anti-β tubulin III (Tuj1) (BAbco, 1:700), mouse anti-synapsin1 (SY SY 1:1000), rabbit anti-β tubulin III (BAbco, 1:2000), mouse anti-O4 (Chemicon, IgM, 1:100), rabbit anti-glial fibrillary acidic protein (DAKO Cytomation, 1:1000). After discarding the primary antibody solution, the slides were rinsed 3 times in PBS, and incubated with secondary antibodies: Cy3-conjugated goat anti-mouse IgG, Fcγ fragment (Jackson ImmunoResearch, West Grove, Pa., 1:1600), Cy5-conjugated goat anti-mouse IgG (Jackson ImmunoResearch, 1:1200), Cy3-conjugated goat anti-rabbit IgG (Jackson ImmunoResearch, 1:1200) and Alexa488-conjugated goat anti-rabbit (Molecular Probes, Eugene, Oreg., 1:1600), secondary antibodies were incubated for 90 minutes at room temperature. The slides were rinsed with PBS, incubated with 300 nM DAPI (4',6-diamidino-2-phenylindole, dihydrochloride) solution (Molecular Probes) for 5 minutes, and finally rinsed and mounted in anti-fading medium (P-7481, Molecular Probes). A Zeiss LSM 510 Meta confocal microscope or an Olympus fluorescent microscope equipped with a digital camera was used to collect images. Imaris Bitplane was applied for 3-D reconstruction of confocal Z-stack images.

In Vivo and in vitro proliferation of choroid plexus cells. For in vivo proliferation test, BrdU (100 mg/kg in 0.9% NaCl) was injected intraperitonealy once a day for 4 weeks prior to sacrifice. For visualization of BrdU-retaining cells, the whole brain was isolated and processed for cryosection, Myosin VIIA and BrdU staining was applied to the cryosections. For in vitro proliferation test, BrdU was added to the CP epithelial cell culture medium 48 hours after initial culture.

Assay for mechanosensory transduction in CP epithelial cells. The animal was sacrificed by cervical dislocation then the choroid plexus of the lateral ventricle was exposed to 5 µM FM1-43FX (Molecular probes) for 60 seconds and fixed with 4% formaldehyde. The thin piece of choroid plexus was mounted to examine the fluorescent intensity to determine dye uptake. To block the entry of FM1-43, the lateral ventricle was pre-incubated and repeatedly flushed with DHS for 4 minutes.

Electrophysiology. Hair cells were identified by the presence of green fluorescence under ultraviolet light. Neural stem cell originated neurons were identified by their distinct neuronal morphology (small, round and phase bright cell body and long uneven processes), spiral ganglion neurons were identified by their much larger round and phase bright cell bodies and unipolar and/or bipolar neurites. The criteria were confirmed by immunostaining in parallel cultures. CNQX (10 µM) was used to block AMPA receptors.

Twenty mice (age range: 5-8 weeks old) were anesthetized with avertin and auditory brainstem response (ABR) measurements were recorded as previously described (Kozel et al. 1998; Flagella et al. 1999). Briefly, a ground needle electrode and recording needle were placed subcutaneously in the scalp, and then a calibrated electrostatic speaker coupled to a hollow ear bar was placed inside the pinna. Broadband clicks and pure tones (8, 16, and 32 kHz) were presented in the animal's ear in 10 dB increments, starting from 0 dB SPL and ending at 100 dB SPL. The ABR sweeps were computer-averaged (time-locked with onset of 128-1024 stimuli, at 20/s) out of the continuous electroencephalographic activity. The threshold of hearing was determined as the lowest intensity of sound required to elicit a characteristic waveform.

Transmission electron microscopy (SEM) Mice were sacrificed by cervical dislocation, lateral wall of lateral ventricle were dissected, fixed with 2.5% glutaraldehyde and 2% paraformaldehyde. For SEM, samples were dehydrated, final dried and infiltrated with gradient Hexamethyldisilazane, mounted and coated with gold. Images were collected on an Philips FEI XL30 SEM. For TEM, samples were post-fixed in 1% osmium tetroxide, dehydrated, infiltrated and polymerized. Ultrathin sections were post-stained. Images were taken on a Philips EM400 TEM with a MegaView digital camera (Soft Imaging Systems, Inc).

Time-lapse microscopy. This procedure was performed using a AxioObserver system (Zeiss) at 37° C. and 5% CO2. Phase-contrast images were collected every 10 min using 10× phase-contrast objectives, and an AxioCamHRm camera (at 1,388×1,040 or 2,776×2,080 pixel resolutions) using Zeiss AxioVision 4.7 software. Mercury (HBO 103 W/2) or Xenon (XBO 75 W/2 OFR, both Osram) lamps were used for fluorescence illumination.

GFP positive hair cells and DiI-labelled choroid plexus cells were detected using FITC and cy3 respectively. Movies for presentation were assembled using Imagej software.

Experiment No. 5 Autologous Transplantation of Choroid Plexus into Hearing Impaired Patients.

Isolation of Choroid Plexus from patient. Choroid plexus (CP) cells are minimally invasively isolated from human patients via occipital horn of lateral ventricle approach under the help of ventriculoscope. The harvested choroid plexus tissue are maintained in ice-cold dissecting solution consisting of Minimum Essential Medium with Hank's salts (Invitrogen), 2% B27, 1% N2 (v/v), and glucose (6 g/L), then digested in an enzyme cocktail containing collagenase-dispase (Roche), DNase I (1 mg/mL) at 37° C. for 20 minutes, then trypsin added to make a final concentration of 0.25%. After incubation for 10 min at 37° C., addition of 50% (v/v) human serum, and gentle trituration, the cell homogenate is centrifuged for 10 min at 700 g.

Assay for mechanosensory transduction of human CP cells. Isolated CP cells are exposed to 5 µM FM1-43FX (Molecular probes) for 60 seconds and fixed with 4% formaldehyde. The thin piece of choroid plexus is mounted to examine the fluorescent intensity to determine dye uptake. To block the entry of FM1-43, the lateral ventricle is pre-incubated and repeatedly flushed with DHS for 4 minutes.

Electrophysiology. Currents are amplified with an amplifier (Axon Instruments) and filtered at a frequency of 2-5 kHz through a low-pass Bessel filter. The data is digitized at 5-500 kHz using an analog-to-digital converter. The extracellular solution for most experiments contained (in mM) NaCl 145, KCl 6, MgCl2 1, CaCl2 0-2, D-glucose 10, and Hepes 10, at pH 7.3. For perforated patch experiments, the tips of the pipettes are filled with an internal solution containing (in mM): KCl 150, Hepes 10, and D-glucose 10, at pH 7.3. The pipettes are front-filled with the internal solution and back-filled with the same solution containing 250 µg/ml amphotericin. The functionality of CP cells is further investigated.

In vitro proliferation of choroid plexus. The CP cell pellet collected from last step is reconstituted with proliferating medium consisting of D-MEM/F-12 with GlutaMAXTM1 (Invitrogen), 2% (v/v) B27, 100 U/ml penicillin, 20 ng/ml EGF, 10 ng/ml FGF-2. Fresh EGF and FGF-2 is added once every other day, and half the culture medium replaced with fresh medium once every 4 days. Two to three weeks later, the cells are concentrated ($10^4$ cell/µl) at ice cold culture medium and ready for autologous transplantation.

Autologous transplantation of CP cells to scala media. The patient is anesthestized and the post-auricle area is depilated and sterilely prepared. An incision is made and extended in the skin posterior and inferior to the auricle. The underlying superficial layer is divided to expose the middle ear space and direct visualization of the cochlear promontory, round window niche, stapedial artery, stapes, and portions of the ossicular chain. This view is sufficient for obtaining intracochlear access via cochleostomy through the promontory and lateral wall into the scala media.

Cochleostomy is performed through the promontory bone and lateral wall of the first cochlear turn. The lateral wall is identified as the region of dark transverse striping along the promontory. A tuberculin syringe prefilled with autologous CP solution is attached to a small needle, which is used to perform the lateral wall cochleostomy. Following puncture through the bony wall, the needle is advanced through the lateral wall and 10 µL of preloaded solution ($10^4$/µl) slowly instilled into the scala media. The needle is withdrawn, and the cochleostomy is quickly sealed with bone wax in a watertight fashion.

The musculature overlying the bony structure is brought together and closed with suture, and the wound is closed deeply and superficially with additional suture. The incision is dressed with antibiotic ointment.

ABR Evaluation. Auditory brainstem response (ABR) and DPOAE measurements is recorded to evaluate hearing rehabilitation. Broadband clicks and pure tones (8, 16, and 32 kHz) are presented in 10 dB increments, starting from 0 dB SPL and ending at 100 dB SPL. The ABR sweeps are computer-averaged (time-locked with onset of 128-1024 stimuli, at 20/s) out of the continuous electroencephalographic activity. The threshold of hearing is determined as the lowest intensity of sound required to elicit a characteristic waveform.

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

TABLE 1

Growth factors secreted by choroid plexus and PCR Primers

| No. | Gene | Primer Sequences (5'-3') | GenBank Acc No., (Product location) | Annealing Temp |
|---|---|---|---|---|
| 1 | MyoVIIA | F: CTCCCTCTACATCGCTCTGTTCG (SEQ ID NO. 5)<br>R: AAGCACCTGCTCCTGCTCGTCCACG (SEQ ID NO. 6) | NM_008663,<br>(4157-4784) | 59° C. |
| 2 | Espin | s2: CAGCCTGAGTCACCGCAGCCTC (SEQ ID NO. 7)<br>as2: TGACCTGTCGCTGCCAGGGCGCG (SEQ ID NO. 8) | NM_207687,<br>2113-2587 | 57° C. |
| 3 | Calretinin | s: AGATCCTGCCGACCGAAGAG (SEQ ID NO. 9)<br>as: AGGGCGTCCAGTTCATTCTC (SEQ ID NO. 10) | NM_007586,<br>338-739 | 54° C. |

TABLE 1-continued

Growth factors secreted by choroid plexus and PCR Primers

| No. | Gene | Primer Sequences (5'-3') | GenBank Acc No., (Product location) | Annealing Temp |
|---|---|---|---|---|
| 4 | CtBP1 | s: CTAGGCATCGCAGTGTGCAATG (SEQ ID NO. 11)<br>as: GGTGGTGGTTGTGCTCATTG (SEQ ID NO. 12) | NM_013502, 488-887 | 54° C. |
| 5 | CtBP2 | s: CAGGACGAGGGCTTCATCAC (SEQ ID NO. 13)<br>as: GCATCACAGAAGGCCACAG (SEQ ID NO. 14) | NM_009980, 200-599 | 52° C. |
| 6 | Math1 | s: GCCCTAACAGCGATGATGG (SEQ ID NO. 15)<br>as: GACCATGAAACGATGCCAC (SEQ ID NO. 16) | NM_007500, 1087-1486 | 54° C. |
| 7 | Brn3c | s: GCAAGAACCCAAATTCTC (SEQ ID NO. 17)<br>as: GGGATCTTAAGATTGGCTAAAG (SEQ ID NO. 18) | NM_138945, 48-653 | 54° C. |
| 8 | NT3 | s: GGTGGGCGAGACTGAATGAC (SEQ ID NO. 19)<br>as: CGTAGTAGCTCTGTGTCCGTTG (SEQ ID NO. 20) | NM_008742, 95-494 | 57° C. |
| 9 | CNTF | s: GAGAAAGGCCGAGTATCCC (SEQ ID NO. 21)<br>as: TAATGCCACCGGGAGACTG (SEQ ID NO. 22) | NM_053007, 1011-1411 | 54° C. |
| 10 | FgF1 | F: ACCGAGAGGTTCAACCTGCC (SEQ ID NO. 23)<br>R: GCCATAGTGAGTCCGAGGACC (SEQ ID NO. 24) | NM_010197, 225-591 | 57° C. |
| 11 | FgF2 | F: AGCGGCTCTACTGCAAGAAC (SEQ ID NO. 25)<br>R: TCGTTTCAGTGCCACATACC (SEQ ID NO. 26) | NM_008006, 86-365 | 54° C. |
| 12 | TGFβ1 | S: CGGACTACTATGCTAAAGAG (SEQ ID NO. 27)<br>as: CGTCAAAAGACAGCCACTCAGG (SEQ ID NO. 28) | NM_011577, 1164-1465 | 51° C. |
| 13 | VEGF | s: GCCGTCCTGTGTGCCGCTGATG (SEQ ID NO. 29)<br>as: GCCCTCCGGACCCAAAGTGCTC (SEQ ID NO. 30) | NM_001025250, 613-1220 | 59° C. |
| 14 | NT4 | s: CCCTGCGTCAGTACTTCTTCGAGAC (SEQ ID NO. 31)<br>as: CTGGACCTCAGGCTCGGCCTGTTC (SEQ ID NO. 32) | NM_198190, 618-866 | 59° C. |
| 15 | IGF1 | s: GGACCAGAGACCCTTTGCGGGG (SEQ ID NO. 33)<br>as: GGCTGCTTTTGTAGGCTTCAGTGG (SEQ ID NO. 34) | NM_010512, 94-303 | 57° C. |
| 16 | IGF2 | s: TCAGTTTGTCTGTTCGGACC (SEQ ID NO. 35)<br>as: ATTGGAAGAACTTGCCCACG (SEQ ID NO. 36) | NM_010514, 1248-1471, | 52° C. |
| 17 | BDNF | s: GCTGCCTTGATGTTTACTTTG (SEQ ID NO. 37)<br>As: CCAGCAGAAAGAGTAGAGGAGG (SEQ ID NO. 38) | X55573, 16-414 | 57° C. |

TABLE 2

Primers for channels markers in choroid plexus

| No. | Gene | Primer Sequences (5'-3') | GenBank Acc No., (Product location) | Annealing Temp |
|---|---|---|---|---|
| 1 | α1D | s: GAGAGATTCCCTTCAGCAGAC (SEQ ID NO. 39)<br>as: GGAAGTAGCCGTGTATCTCAG (SEQ ID NO. 40) | NM_028981, 5164-5573 | 54° C. |
| 2 | BK | s: TTGTTATGGTGATCTGTTCTGC (SEQ ID NO. 41)<br>as: GGCTTGATTTGAATGTTTCTGG (SEQ ID NO. 42) | NM_010610, 3431-3830 | 51° C. |
| 3 | KCNQ4 | s: AAAGACCGAATCCGCATAAG (SEQ ID NO. 43)<br>As: GGTGTCCTGCTGAATACTGCTC (SEQ ID NO. 44) | AK163659, 1099-1498 | 51° C. |
| 4 | SK2 | s: ACCACCAGCATCACCAACC (SEQ ID NO. 45)<br>as: GGAGAGACTGATAAGGCATTTC (SEQ ID NO. 46) | AY123778, 17-591 | 52° C. |

References

1. Ernfors, P., Duan, M. L., ElShamy, W. M., Canlon, B. (1996) Protection of auditory neurons from aminoglycoside toxicity by neurotrophin-3. Nat Med 2: 463-467.

2. Li, H., Roblin, G., Liu, H., Heller, S. (2003) Generation of hair cells by stepwise differentiation of embryonic stem cells. Proc Natl Acad Sci USA 100: 13495-13500.

3. Izumikawa, M., Minoda, R., Kawamoto, K., Abrashkin, K. A., Swiderski, D. L., Dolan, D. F., Brough, D. E., Raphael, Y. (2005) Auditory hair cell replacement and hearing improvement by Atoh1 gene therapy in deaf mammals. Nat Med 11: 271-276.
4. Shou, J., Zheng, J. L., Gao, W. Q. (2003) Robust generation of new hair cells in the mature mammalian inner ear by adenoviral expression of Hath1. Mol Cell Neurosci 23: 169-179.
5. Wei, D., Jin, Z., Jarlebark, L., Scarfone, E., Ulfendahl, M. (2007) Survival, synaptogenesis, and regeneration of adult mouse spiral ganglion neurons in vitro. Dev Neurobiol 67: 108-122.
6. Jeon, S. J., Oshima, K., Heller, S., Edge, A. S. (2007) Bone marrow mesenchymal stem cells are progenitors in vitro for inner ear hair cells. Mol Cell Neurosci 34: 59-68.
7. Nakagawa, T., Ito, J. (2005) Cell therapy for inner ear diseases. Curr Pharm Des 11: 1203-1207.
8. Doyle, K. L., Kazda, A., Hort, Y., McKay, S. M., Oleskevich, S. (2007) Differentiation of adult mouse olfactory precursor cells into hair cells in vitro. Stem Cells 25: 621-627.
9. Gage, F. H. (2000) Mammalian neural stem cells. Science 287: 1433-1438.
10. Doetsch, F., Caille, I., Lim, D. A., Garcia-Verdugo, J. M., Alvarez-Buylla, A. (1999) Subventricular zone astrocytes are neural stem cells in the adult mammalian brain. Cell 97: 703-716.
11. Laywell, E. D., Rakic, P., Kukekov, V. G., Holland, E. C., Steindler, D. A. (2000) Identification of a multipotent astrocytic stem cell in the immature and adult mouse brain. Proc Natl Acad Sci USA 97: 13883-13888.
12. Morshead, C. M., Garcia, A. D., Sofroniew, M. V., van Der Kooy, D. (2003) The ablation of glial fibrillary acidic protein-positive cells from the adult central nervous system results in the loss of forebrain neural stem cells but not retinal stem cells. Eur J Neurosci 18: 76-84.
13. Sanai, N., Tramontin, A. D., Quinones-Hinojosa, A., Barbaro, N. M., Gupta, N., Kunwar, S., Lawton, M. T., McDermott, M. W., Parsa, A. T., Manuel-Garcia Verdugo, J., Berger, M. S., Alvarez-Buylla, A. (2004) Unique astrocyte ribbon in adult human brain contains neural stem cells but lacks chain migration. Nature 427: 740-744.
14. Stankovic, K., R10, C., Xia, A., Sugawara, M., Adams, J. C., Liberman, M. C., Corfas, G. (2004) Survival of adult spiral ganglion neurons requires erbB receptor signaling in the inner ear. J Neurosci 24: 8651-8661.
15. Zecevic, N. (2004) Specific characteristic of radial glia in the human fetal telencephalon. Glia 48: 27-35.
16. Johansson, C. B., Momma, S., Clarke, D. L., Risling, M., Lendahl, U., Frisen, J. (1999) Identification of a neural stem cell in the adult mammalian central nervous system. Cell 96: 25-34.
17. Ke, Y., Chi, L., Xu, R., Luo, C., Gozal, D., Liu, R. (2006) Early response of endogenous adult neural progenitor cells to acute spinal cord injury in mice. Stem Cells 24: 1011-1019.
18. Zhang, R. L., Zhang, Z. G., Wang, Y., LeTourneau, Y., Liu, X. S., Zhang, X., Gregg, S. R., Wang, L., Chopp, M. (2007) Stroke induces ependymal cell transformation into radial glia in the subventricular zone of the adult rodent brain. J Cereb Blood Flow Metab 27: 1201-1212.
19. Spassky, N., Merkle, F. T., Flames, N., Tramontin, A. D., Garcia-Verdugo, J. M., Alvarez-Buylla, A. (2005) Adult ependymal cells are postmitotic and are derived from radial glial cells during embryogenesis. J Neurosci 25: 10-18.
20. Chiasson, B. J., Tropepe, V., Morshead, C. M., van der Kooy, D. (1999) Adult mammalian forebrain ependymal and subependymal cells demonstrate proliferative potential, but only subependymal cells have neural stem cell characteristics. J Neurosci 19: 4462-4471.
21. Boeda, B., Weil, D., Petit, C. (2001) A specific promoter of the sensory cells of the inner ear defined by transgenesis. Hum Mol Genet 10: 1581-1589.
22. Hasson, T., Gillespie, P. G., Garcia, J. A., MacDonald, R. B., Zhao, Y., Yee, A. G., Mooseker, M. S., Corey, D. P. (1997) Unconventional myosins in inner-ear sensory epithelia. J Cell Biol 137: 1287-1307.
23. Zheng, J. L., Gao, W. Q. (2000) Overexpression of Math1 induces robust production of extra hair cells in postnatal rat inner ears. Nat Neurosci 3: 580-586.
24. Ming, G. L., Song, H. (2005) Adult neurogenesis in the mammalian central nervous system. Annu Rev Neurosci 28: 223-250.
25. Knirsch, M., Brandt, N., Braig, C., Kuhn, S., Hirt, B., Munkner, S., Knipper, M., Engel, J. (2007) Persistence of Ca(v)1.3 Ca2+ channels in mature outer hair cells supports outer hair cell afferent signaling. J Neurosci 27: 6442-6451.
26. Meyers, J. R., MacDonald, R. B., Duggan, A., Lenzi, D., Standaert, D. G., Corwin, J. T., Corey, D. P. (2003) Lighting up the senses: FM1-43 loading of sensory cells through nonselective ion channels. J Neurosci 23: 4054-4065.
27. Si, F., Brodie, H., Gillespie, P. G., Vazquez, A. E., Yamoah, E. N. (2003) Developmental assembly of transduction apparatus in chick basilar papilla. J Neurosci 23: 10815-10826.
28. Glowatzki, E., Fuchs, P. A. (2002) Transmitter release at the hair cell ribbon synapse. Nat Neurosci 5: 147-154.
29. Martinez-Monedero, R., Corrales, C. E., Cuajungco, M. P., Heller, S., Edge, A. S. (2006) Reinnervation of hair cells by auditory neurons after selective removal of spiral ganglion neurons. J Neurobiol 66: 319-331.
30. Retzius, G. (1893) Zur Entwicklung der Zellen des Ganglion Spirale Acustici and zur Endigungsweise des Gehornerven bei den Saugethieren. Biol. Untersuch. 4: 52-57.
31. Huang, L. C., Thorne, P. R., Housley, G. D., Montgomery, J. M. (2007) Spatiotemporal definition of neurite outgrowth, refinement and retraction in the developing mouse cochlea. Development 134: 2925-2933.
32. Nichols, C. G., Lopatin, A. N. (1997) Inward rectifier potassium channels Annu Rev Physiol 59: 171-191.
33. Zheng, J. L., Keller, G., Gao, W. Q. (1999) Immunocytochemical and morphological evidence for intracellular self-repair as an important contributor to mammalian hair cell recovery. J Neurosci 19: 2161-2170.
34. Gale, J. E., Meyers, J. R., Periasamy, A., Corwin, J. T. (2002) Survival of bundleless hair cells and subsequent bundle replacement in the bullfrog's saccule. J Neurobiol 50: 81-92.
35. Warchol, M. E., Lambert, P. R., Goldstein, B. J., Forge, A., Corwin, J. T. (1993) Regenerative proliferation in inner ear sensory epithelia from adult guinea pigs and humans. Science 259: 1619-1622.
36. Bermingham, N. A., Hassan, B. A., Price, S. D., Vollrath, M. A., Ben-Arie, N., Eatock, R. A., Bellen, H. J., Lysakowski, A., Zoghbi, H. Y. (1999) Math1: an essential gene for the generation of inner ear hair cells. Science 284: 1837-1841.
37. Lim, D. A., Tramontin, A. D., Trevejo, J. M., Herrera, D. G., Garcia-Verdugo, J. M., Alvarez-Buylla, A. (2000) Noggin antagonizes BMP signaling to create a niche for adult neurogenesis. Neuron 28: 713-726.
38. Ishibashi, M., Ang, S. L., Shiota, K., Nakanishi, S., Kageyama, R., Guillemot, F. (1995) Targeted disruption of mammalian hairy and Enhancer of split homolog-1 (HES- 1) leads to up-regulation of neural helix-loop-helix factors, premature neurogenesis, and severe neural tube defects. Genes Dev 9: 3136-3148.
39. Li, H., Liu, H., Heller, S. (2003) Pluripotent stem cells from the adult mouse inner ear. Nat Med 9: 1293-1299.
40. Hasson, T., Heintzelman, M. B., Santos-Sacchi, J., Corey, D. P., Mooseker, M. S. (1995) Expression in cochlea and retina of myosin VIIa, the gene product defective in Usher syndrome type 1B. Proc Natl Acad Sci USA 92: 9815-9819.
41. Fritzsch, B., Silos-Santiago, I., Bianchi, L. M., Farinas, I. (1997) Effects of neurotrophin and neurotrophin receptor disruption on the afferent inner ear innervation. Semin Cell Dev Biol 8: 277-284.
42. Hu, Z., Wei, D., Johansson, C. B., Holmstrom, N., Duan, M., Frisen, J., Ulfendahl, M. (2005) Survival and neural differentiation of adult neural stem cells transplanted into the mature inner ear. Exp Cell Res 302: 40-47.
43. Regala, C., Duan, M., Zou, J., Salminen, M., Olivius, P. (2005) Xenografted fetal dorsal root ganglion, embryonic stem cell and adult neural stem cell survival following implantation into the adult vestibulocochlear nerve. Exp Neurol 193: 326-333.
44. Shihabuddin, L. S., Horner, P. J., Ray, J., Gage, F. H. (2000) Adult spinal cord stem cells generate neurons after transplantation in the adult dentate gyrus. J Neurosci 20: 8727-8735.
45. Alvarez-Buylla, A., Lim, D. A. (2004) For the long run: maintaining germinal niches in the adult brain. Neuron 41: 683-686.
46. Song, H. J., Stevens, C. F., Gage, F. H. (2002) Neural stem cells from adult hippocampus develop essential properties of functional CNS neurons. Nat Neurosci 5: 438-445.
47. Roehm, P. C., Hansen, M. R. (2005) Strategies to preserve or regenerate spiral ganglion neurons. Curr Opin Otolaryngol Head Neck Surg 13: 294-300.
48. Levic, S., Nie, L., Tuteja, D., Harvey, M., Sokolowski, B. H., Yamoah, E. N. (2007) Development and regeneration of hair cells share common functional features. Proc Natl Acad Sci USA 104: 19108-19113.
49. Borlongan C V, Skinner S J, Geaney M, Vasconcellos A V, Elliott R B, Emerich D F (2004) Intracerebral transplantation of porcine choroid plexus provides structural and functional neuroprotection in a rodent model of stroke. Stroke 35:2206-2210.
50. Breier G, Albrecht U, Sterrer S, Risau W (1992) Expression of vascular endothelial growth factor during embryonic angiogenesis and endothelial cell differentiation. Development 114:521-532.
51. Doyle K L, Kazda A, Hort Y, McKay S M, Oleskevich S (2007) Differentiation of adult mouse olfactory precursor cells into hair cells in vitro. Stem Cells 25:621-627.
52. Emerich D F, Schneider P, Bintz B, Hudak J, Thanos C G (2007) In vitro exposure of cultured porcine choroid plexus epithelial cells to immunosuppressant, anti-inflammatory, and psychoactive drugs. Cell Transplant 16:435-440.
53. Emerich D F, Thanos C G, Goddard M, Skinner S J, Geany M S, Bell W J, Bintz B, Schneider P, Chu Y, Babu R S, Borlongan C V, Boekelheide K, Hall S, Bryant B, Kordower J H (2006) Extensive neuroprotection by choroid plexus transplants in excitotoxin lesioned monkeys. Neurobiol Dis 23:471-480.
54. Gale J E, Marcotti W, Kennedy H J, Kros C J, Richardson G P (2001) FM1-43 dye behaves as a permeant blocker of the hair-cell mechanotransducer channel. J Neurosci 21:7013-7025.
55. Ide C, Kitada M, Chakrabortty S, Taketomi M, Matsumoto N, Kikukawa S, Mizoguchi A, Kawaguchi S, Endoh K, Suzuki Y (2001) Grafting of choroid plexus ependymal cells promotes the growth of regenerating axons in the dorsal funiculus of rat spinal cord: a preliminary report. Exp Neurol 167:242-251.
56. Izumikawa M, Minoda R, Kawamoto K, Abrashkin K A, Swiderski D L, Dolan D F, Brough D E, Raphael Y (2005) Auditory hair cell replacement and hearing improvement by Atoh1 gene therapy in deaf mammals. Nat Med 11:271-276.
57. Kros C J, Marcotti W, van Netten S M, Self T J, Libby R T, Brown S D, Richardson G P, Steel K P (2002) Reduced climbing and increased slipping adaptation in cochlear hair cells of mice with Myo7a mutations. Nat Neurosci 5:41-47.
58. Li H, Liu H, Heller S (2003) Pluripotent stem cells from the adult mouse inner ear. Nat Med 9:1293-1299.
59. Shou J, Zheng J L, Gao W Q (2003) Robust generation of new hair cells in the mature mammalian inner ear by adenoviral expression of Hath1. Mol Cell Neurosci 23:169-179.
60. Wei D, Jin Z, Jarlebark L, Scarfone E, Ulfendahl M (2007) Survival, synaptogenesis, and regeneration of adult mouse spiral ganglion neurons in vitro. Dev Neurobiol 67:108-122.
61. D, Blanchard S, Kaplan J, Guilford P, Gibson F, Walsh J, Mburu P, Varela A, Levilliers J, Weston M D, et al. (1995) Defective myosin VIIA gene responsible for Usher syndrome type 1B. Nature 374:60-61.
62. Gurney K J, Estrada E Y, Rosenberg G A (2006) Blood-brain barrier disruption by stromelysin-1 facilitates neutrophil infiltration in neuroinflammation. Neurobiol Dis 23:87-96.
63. Kakigi A, Takeda T (1998) Effect of artificial endolymph injection into the cochlear duct on the endocochlear potential. Hear Res 116:113-118.
64. Kim T S, Nakagawa T, Endo T, Iguchi F, Murai N, Naito Y, Ito J (2002) Alteration of E-cadherin and beta-catenin in mouse vestibular epithelia during induction of apoptosis. Neurosci Lett 329:173-176.
65. Lohmann C, Krischke M, Wegener J, Galla H J (2004) Tyrosine phosphatase inhibition induces loss of blood-brain barrier integrity by matrix metalloproteinase-dependent and -independent pathways. Brain Res 995:184-196.
66. Olivius P, Alexandrov L, Miller J, Ulfendahl M, Bagger-Sjoback D, Kozlova E N (2003) Allografted fetal dorsal root ganglion neuronal survival in the guinea pig cochlea. Brain Res 979:1-6.
67. Oshima K, Grimm C M, Corrales C E, Senn P, Martinez Monedero R, Geleoc G S, Edge A, Holt J R, Heller S (2007) Differential distribution of stem cells in the auditory and vestibular organs of the inner ear. J Assoc Res Otolaryngol 8:18-31.
68. Strazielle N, Khuth S T, Murat A, Chalon A, Giraudon P, Belin M F, Ghersi-Egea J F (2003) Pro-inflammatory cytokines modulate matrix metalloproteinase secretion and organic anion transport at the blood-cerebrospinal fluid barrier. J Neuropathol Exp Neurol 62:1254-1264.
69. Takahashi K, Tanabe K, Ohnuki M, Narita M, Ichisaka T, Tomoda K, Yamanaka S (2007) Induction of pluripotent stem cells from adult human fibroblasts by defined factors. Cell 131:861-872.
70. Vats A, Tolley N S, Polak J M, Buttery L D (2002) Stem cells: sources and applications. Clin Otolaryngol Allied Sci 27:227-232.
71. Wei D, Levic S, Nie L, Gao W Q, Petit C, Jones E G, Yamoah E N (2008) Cells of adult brain germinal zone 72. Weil D, Blanchard S, Kaplan J, Guilford P, Gibson F, Walsh J, Mburu P, Varela A, Levilliers J, Weston M D, et al. (1995) Defective myosin VIIA gene responsible for Usher syndrome type 1B. Nature 374:60-61.
73. Yang Y, Estrada E Y, Thompson J F, Liu W, Rosenberg G A (2007) Matrix metalloproteinase-mediated disruption of tight junction proteins in cerebral vessels is reversed by synthetic matrix metalloproteinase inhibitor in focal ischemia in rat. J Cereb Blood Flow Metab 27:697-709.
74. Yu J, Hu K, Smuga-Otto K, Tian S, Stewart R, Slukvin, I I, Thomson J A (2009) Human induced pluripotent stem cells free of vector and transgene sequences. Science 324: 797-801.

The invention claimed is:

1. An isolated ependymal cell, wherein the cell expresses the marker myosin VIIA and does not express glial fibrillary acidic protein (GFAP) and does not express at least one neuronal marker of the group of TuJ1, Hes1, NeuN, or neurofilament.
2. The isolated ependymal cell of claim 1, wherein the cell is isolated from the lateral ventricle or the choroid plexus of a subject.
3. The isolated ependymal cell of claim 2, wherein the subject is a murine, a rat, a bovine, a simian, a porcine or a human.
4. The isolated ependymal cell of claim 1, wherein the cell further expresses one or more of the markers F-actin, ribeye or myosin VI.
5. The isolated ependymal cell of claim 1, wherein the cell is an isolated ciliated epithelial cell.
6. The isolated ependymal cell of claim 1, wherein the cell is an isolated polarized ependymal cell.
7. The isolated ependymal cell of claim 1, wherein the cell can establish synapse-like contact with a spiral ganglia neuron (SGN).
8. A population of isolated ependymal cells of claim 1 or 4.
9. An expanded clonal population of ependymal cells of claim 8.
10. A composition comprising the isolated cell of claim 1, and a carrier.
11. The composition of claim 10, wherein the carrier is a pharmaceutically acceptable carrier.
12. The composition of claim 10, further comprising an isolated neural stem cell (NSC) or a NSC-derived neuron.
13. The composition of claim 10, further comprising an isolated spiral ganglia-like neuron (SGN).
14. The composition of claim 10, further comprising an isolated hair cell (HC).
15. The isolated ependymal cell of claim 1, wherein the cell is isolated from the subventricular zone (SVZ) of the lateral ventricle (LV).
16. The isolated ependymal cell of claim 1, wherein the cell expresses synapsin 1.
17. The isolated ependymal cell of claim 1, wherein the cell can establish synaptic contact with a hair cell (HC) or a spiral ganglia neuron (SGN).
18. A population of isolated ependymal cells of claim 1.
19. An expanded clonal population of ependymal cells of claim 1.
20. An isolated ependymal cell of claim 1 or 4, further comprising one or more of a label, a detectable label or an exogenous polynucleotide.
21. A method for identifying an ependymal cell of claim 1, comprising screening a composition that may contain the cell for the expression of myosin VIIA, and optionally for expression of a gene or protein selected from the group consisting of F-actin, ribeye and myosin VI and the combinations thereof, and screening for the lack of expression of glial fibrillary acidic protein (GFAP) and lack of expression of at least one neuronal marker of the group of TuJ1, Hes1, NeuN, a Neurofilament or combinations thereof.

* * * * *